US010736877B2

(12) United States Patent
Kerr et al.

(10) Patent No.: US 10,736,877 B2
(45) Date of Patent: Aug. 11, 2020

(54) TRYPTAMINE-BASED SHIP INHIBITORS FOR THE TREATMENT OF CANCER

(71) Applicants: THE RESEARCH FOUNDATION FOR THE STATE UNIVERSITY OF NEW YORK, Syracuse, NY (US); SYRACUSE UNIVERSITY, Syracuse, NY (US)

(72) Inventors: William G. Kerr, Syracuse, NY (US); Sandra Fernandes Denney, Constantia, NY (US); John D. Chisholm, Fayetteville, NY (US)

(73) Assignees: SYRACUSE UNIVERSITY, Syracuse, NY (US); THE RESEARCH FOUNDATION FOR THE STATE UNIVERSITY of New York, Syracuse, NY (US)

(*) Notice: Subject to any disclaimer, the term of this patent is extended or adjusted under 35 U.S.C. 154(b) by 0 days.

(21) Appl. No.: 15/396,272

(22) Filed: Dec. 30, 2016

(65) Prior Publication Data

US 2017/0189380 A1 Jul. 6, 2017

Related U.S. Application Data

(60) Provisional application No. 62/273,779, filed on Dec. 31, 2015.

(51) Int. Cl.
*A61K 31/4045* (2006.01)
*A61P 3/10* (2006.01)
*A61P 35/00* (2006.01)

(52) U.S. Cl.
CPC ............ *A61K 31/4045* (2013.01); *A61P 3/10* (2018.01); *A61P 35/00* (2018.01)

(58) Field of Classification Search
CPC ..... A61K 31/4045; C07D 209/40; A61P 3/10; A61P 35/00
See application file for complete search history.

(56) References Cited

U.S. PATENT DOCUMENTS

| 2,995,567 | A | * | 8/1961 | Sarett | C07D 209/10 548/455 |
|---|---|---|---|---|---|
| 3,074,960 | A | | 1/1963 | Archer | |
| 3,478,054 | A | * | 11/1969 | Pattison | C07D 209/16 548/504 |
| 5,710,143 | A | | 1/1998 | Suzuki et al. | |
| 9,447,139 | B2 | | 9/2016 | Kerr et al. | |
| 2009/0286847 | A1 | * | 11/2009 | Fang | A61K 31/404 514/415 |
| 2012/0178725 | A1 | | 7/2012 | Kerr | |
| 2012/0183600 | A1 | * | 7/2012 | Chen | A61K 31/155 424/450 |
| 2016/0129017 | A1 | | 5/2016 | Kerr et al. | |

FOREIGN PATENT DOCUMENTS

| EP | 0375133 A1 | 6/1990 |
|---|---|---|
| WO | 2007062399 A2 | 5/2007 |
| WO | 2010045199 A2 | 4/2010 |
| WO | 2011060976 A1 | 5/2011 |
| WO | 2011069118 A1 | 6/2011 |
| WO | 2015003003 A1 | 1/2015 |

OTHER PUBLICATIONS

Benanserine (CAS reg. No. 441-91-8), retrieved from SNT on Apr. 1, 2019. (Year: 2019).*
Annis et al. (Sep. 1, 2009) "Inhibitors of the Lipid Phosphatase SHIP2 Discovered by High Throughput Affinity Selection-Mass Spectrometry Screening of Combinatorial Libraries," Combinatorial Chemistry and High Throughput Screening. 12(8):760-771.
Bar-Yehuda et al. (Dec. 2002) "Agonists to the A3 adenosine receptor induce G-CSF production via NF-KB activation," Experimental Hematology. 30(12):1390-1398.
Brooks et al. (Apr. 1, 2010) "SHIP1 inhibition increases immunoregulatory capacity and triggers apoptosis of hematopoietic cancer cells," J Immunol. 184(7):3582-9.
Fuhler et al. (2012) "Therapeutic potential of SH2 domain-containing inositol-5'-phosphatase 1 (SHIP1) and SHIP2 inhibition in cancer," Mol. Med. 18(1):65-75.
Ghansah et al. (2004) "Expansion of myeloid suppressor cells in SHIP deficient mice represses allogeneic T cell responses," J Immunol. 173:7324-7330.
Hazen et al. (2009) "SHIP is required for a functional hematopoietic stem cell niche," Blood. 113:2924-2933.
Hunter et al. (2004) "Loss of SHIP and CIS recruitment to the granulocyte colony-stimulating factor receptor contribute to hyperproliferative responses in severe congenital neutropenia/acute myelogenous leukemia," J Immunol. 173:5036-5045.
Iyer et al. (Mar. 2013) "Role of SHIP1 in bone biology," Ann NY Arad Sci. 1280:11-14.
Iyer et al. (May 24, 2014) "SHIP1 Regulates MSC Numbers and Their Osteolineage Commitment by Limiting Induction of the PI3K/Akt/13-Catenin/Id2 Axis," Stem Cells Dev. 23(19):2336-2351.
Kerr (2008) "A role for SHIP in stem cell biology and transplantation," Curr Stem Cell Res Ther. 3:99-106.
Kerr et al. (2010) "SHIP deficiency causes Crohn's disease-like ileitis," Gut. 60:177-188.
Khedkar et al. (Apr. 5, 2004) "Efficient one-pot synthesis of tryptamines and tryptamine homologues by amination of chloroalkynes," Tetrahedron Letters. 45(15):3123-3126.
Salikov et al. (Jun. 27, 2015) "Synthesis and cytotoxic properties of tryptamine derivatives," Bioorganic & Medicinal Chemistry Letters. 25(17):3597-3600.
Seshacharyulu et al. (2012) "Targeting the EGFR signaling pathway in cancer therapy," Expert Opinion on Therapeutic Targets. pp. 15-31.

(Continued)

*Primary Examiner* — Theodore R. West
(74) *Attorney, Agent, or Firm* — Lathrop GPM LLP

(57) ABSTRACT

The present disclosure provides compositions that inhibit the SH2-containing inositol 5'-phosphatase (SHIP), as well as methods using such compositions for use in treating or ameliorating the effects of a medical condition in a subject.

5 Claims, 9 Drawing Sheets

(56) References Cited

OTHER PUBLICATIONS

Suwa et al. (Oct. 19, 2009) "Discovery and Functional Characterization of a Novel Small Molecule Inhibitor of the Intracellular Phosphatase, SHIP2," British Journal of Pharmacology. 158(3):879-887.
Viernes et al. (2014) "Discovery and development of small molecule SHIP phosphatase modulators," Med Res Rev. 34(4):795-824.
Wong et al. (2010) "Targeting the PI3K signaling pathway in cancer," Current Opinion in Genetics and Development. pp. 87-90.
International Search Report corresponding to International Patent Application No. PCT/US2016/069605, dated Mar. 8, 2017.

* cited by examiner

Fig. 7A MDSC Spleen
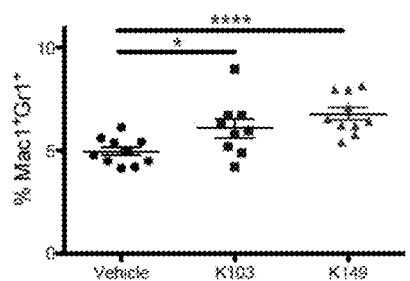
Fig. 7B iTregs Spleen
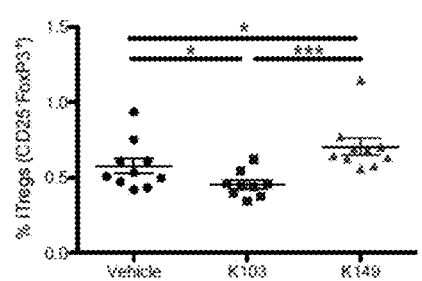
Fig. 7C nTregs Spleen
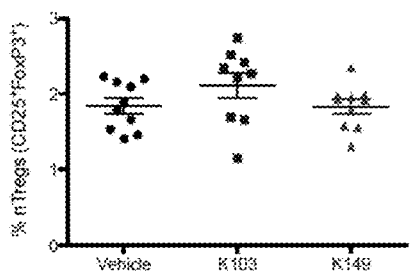
Fig. 7D Neutrophils
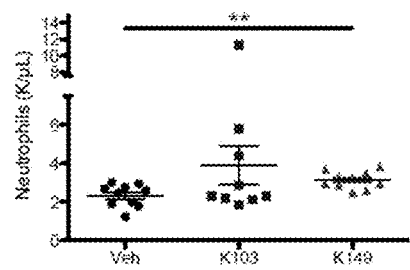
7 days IP 5% DMSO in saline 10mg/kg, One-tailed t-test, *p<0.05,  p<0.01, *p<0.001, ****p<0.0001

TRYPTAMINE-BASED SHIP INHIBITORS FOR THE TREATMENT OF CANCER

CROSS-REFERENCE TO RELATED APPLICATIONS

This application claims the benefit of U.S. Provisional Application No. 62/273,779, filed on Dec. 31, 2015, the content of which is incorporated herein by reference in its entirety.

STATEMENT REGARDING FEDERALLY SPONSORED RESEARCH

This invention was made with government support under contract nos. 5R01HL085580; 5R01HL07252312; and 5R01HL10712704 awarded by the National Institutes of Health. The government has certain rights in the invention.

BACKGROUND OF THE DISCLOSURE

Colorectal cancer (CRC) is the second most common malignancy in women and the third most common malignancy in men worldwide (1). Although CRC mortality has been declining due to improvements in screening techniques and CRC treatment, it is still the second most common cause of cancer-related death. Therapeutic approaches for CRC have included antimetabolite drugs interfering in biosynthetic processes. However, these compounds do not specifically target cancer cells alone, resulting in a number of side-effects. More specific targeted therapies have also been used. In particular, inhibitors of the Epidermal Growth Factor Receptor (EGFR) have been used (2-4). EGFR is a kinase, whose activity results in phosphorylation and activation of downstream signaling cascades such as the Ras-Raf-MEK-ERK and PI3K-PKB/Akt pathways (5). However, some CRCs harbor an activating mutation in the Ras gene (6), rendering the use of upstream EGFR inhibitors ineffective (7). Pan-kinase inhibitors (e.g. Regorafenib (8)) or selective kinase inhibitors (e.g. PI3K/AKT inhibitors (9)) are currently being tested, however, the potential for side effects is present as phosphorylation of proteins and lipids is essential for virtually all cellular functions. While kinases have so far been targeted for treatment, phosphatases are generally regarded as tumor suppressors and have for the most part been disregarded in cancer research.

SUMMARY OF THE DISCLOSURE

The present disclosure provides compositions comprising small molecules which inhibit the SH2-containing inositol 5'-phosphatase-2 (SHIP2), for use in treating or ameliorating the effects of a medical condition (e.g., cancer) in a subject. Examples of cancers that the present compositions can be used for include colorectal cancer and breast cancer.

The compounds of the present disclosure may be used to treat or ameliorate obesity and/or conditions or symptoms associated therewith.

In an aspect, the present invention relates to a method for inhibiting the growth of cancer cells, the method comprising contacting cancer cells with a therapeuticly effective or prophylactically effect amount of a composition comprising a compound having the following structure:

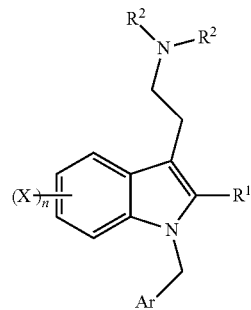

wherein, Ar is a $C_{5-6}$ aryl, $R^1$ is selected from the group consisting of H, $C_{1-4}$ alkyl, and $C_{5-6}$ aryl, each $R^2$ is independently selected from the group consisting of H, $C_{1-4}$ alkyl, and $C_{5-6}$ aryl, each X, if present, is independently selected from the group consisting of halo, $C_{1-4}$ alkyl, $C_{5-6}$ aryl, and —Y—$R^3$, where Y is selected from the group consisting of —S—, —NH—, —O—, $R^3$ is H or $C_{1-4}$ alkyl, and n is 0-4.

In another aspect, the present invention relates to a method for inhibiting a SH2-containing inositol 5'-phosphatase (SHIP) in a subject, the method comprising administering to the subject a composition comprising an effective amount of a compound having the following structure:

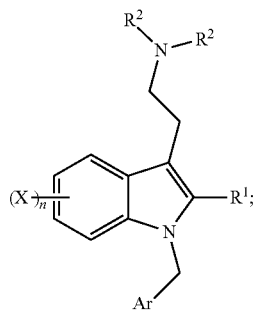

wherein,

Ar is a $C_{5-6}$ aryl;

$R^1$ is selected from the group consisting of H, $C_{1-4}$ alkyl, and $C_{5-6}$ aryl;

each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;

wherein Y is selected from the group consisting of —S—, —NH—, —O—; and $R^3$ is H or $C_{1-4}$ alkyl; and n is 0-4, and pharmaceutically acceptable esters, salts, and prodrugs thereof.

In an aspect, the present invention relates to a composition for use in inhibiting a SH2-containing inositol 5'-phosphatase (SHIP) in a subject, the composition comprising a compound having the following structure:

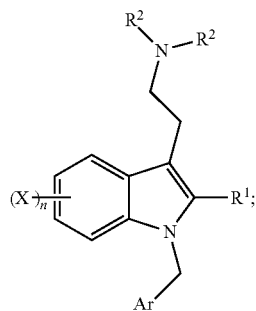

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;
each X, if present, is independently selected from the group consisting of halo, $C_{1-4}$ alkyl, $C_{5-6}$ aryl, and —Y—$R^3$;
  wherein Y is selected from the group consisting of —S—, —NH—, —O—; and
  $R^3$ is H or $C_{1-4}$ alkyl; and
n is 0-4, and pharmaceutically acceptable esters, salts, and prodrugs thereof.

In another aspect, the present invention relates to a method for inhibiting a SH2-containing inositol 5′-phosphatase (SHIP) in a mammalian cell, the method comprising administering to the cell a composition comprising an effective amount of a compound having the following structure:

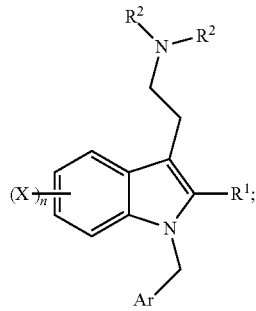

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;
each X, if present, is independently selected from the group consisting of halo, $C_{1-4}$ alkyl, $C_{5-6}$ aryl, and —Y—$R^3$;
  wherein Y is selected from the group consisting of —S—, —NH—, —O—; and
  $R^3$ is H or $C_{1-4}$ alkyl; and
n is 0-4, and pharmaceutically acceptable esters, salts, and prodrugs thereof.

In another aspect, the present invention relates to a composition for use in inhibiting activity associated with SH2-containing inositol 5′-phosphatase (SHIP) in a mammalian cell, the composition comprising a compound having the following structure:

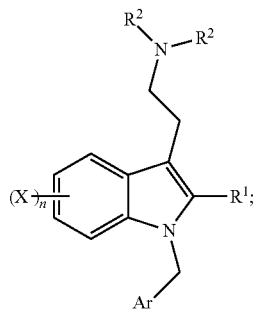

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;
each X, if present, is independently selected from the group consisting of halo, $C_{1-4}$ alkyl, $C_{5-6}$ aryl, and —Y—$R^3$;
  wherein Y is selected from the group consisting of —S—, —NH—, —O—; and
  $R^3$ is H or $C_{1-4}$ alkyl; and
n is 0-4, and pharmaceutically acceptable esters, salts, and prodrugs thereof.

In a further aspect, the present invention relates to a pharmaceutical composition comprising an effective amount of a compound having the following structure:

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;
each X, if present, is independently selected from the group consisting of halo, $C_{1-4}$ alkyl, $C_{5-6}$ aryl, and —Y—$R^3$;
  wherein Y is selected from the group consisting of —S—, —NH—, —O—; and
  $R^3$ is H or $C_{1-4}$ alkyl; and
n is 0-4, and pharmaceutically acceptable esters, salts, and prodrugs thereof.

BRIEF DESCRIPTION OF THE FIGURES

FIGS. 7A-D are graphs depicting the effect of K149 on MDSC FIG. 7A, iTreg cells FIG. 7B, nTreg cells FIG. 7C, and neutrophils FIG. 7D.

DESCRIPTION OF THE DISCLOSURE

Figure 1A:
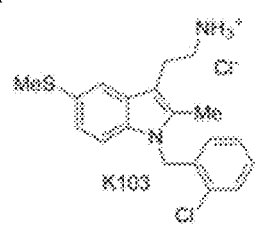
FIGS. 1A and 1B shows the structure of K103 and K149 compounds, respectively, used to perform Malachite Phosphatase Release Assay (Echelon) performed on recombinant human tSHIP1 (see FIG. 1C) and tSHIP2 (see FIG. 1D) at indicated doses. Compounds were dissolved in 100% DMSO and then diluted to indicate final concentrations of performed assays (5% DMSO final concentration). Bar graphs in FIG. 1C and FIG. 1D show the activity, measured as relative to solvent only control (0 µM), from triplicate wells from at least two independent experiments.

The "SHIP inhibitors" of the present invention are also referred to herein as "SHIP inhibitor compounds," "SHIP1 inhibitors," "SHIP1 inhibitor compounds," "SHIP2 inhibitors," SHIP2 inhibitor compounds," "pan-SHIP1/2 inhibitors," and the like. In one embodiment, the SHIP inhibitor compounds of the present invention are selective inhibitors of SHIP2.

As used herein, the term "alkyl group," unless otherwise stated, refers to a $C_1$-$C_4$ branched or unbranched hydrocarbons. Examples of such alkyl groups include methyl groups, ethyl groups, propyl groups, butyl groups, isopropyl groups, sec-butyl, and tert-butyl groups. For example, the alkyl group can be a $C_1$-$C_4$ alkyl group including all integer numbers of carbons and ranges of numbers of carbons there between. The alkyl group can be unsubstituted or substituted with various substituents which may be the same or different.

As used herein, the term "aryl group," unless otherwise stated, refers to a $C_5$-$C_6$ aromatic carbocyclic group. The aryl group can be unsubstituted or substituted with various substituents which may be the same or different. A non-limiting example of a suitable aryl group includes phenyl.

As used herein, the term "halo group," unless otherwise stated, refers to fluoro, chloro, bromo and iodo.

The term "inositol polyphosphate 5-phosphatase" as used herein refers to a family of phosphatases each of which removes the 5' phosphate from inositol- and phosphatidylinositol-polyphosphates.

The term "SHIP" as used herein refers to SH2-containing inositol-5-phosphatase.

A "therapeutically effective amount" describes an amount that will generate the desired therapeutic outcome (i.e., achieve therapeutic efficacy). For example, a therapeutically effective dose of a compound of the present disclosure is an amount that is sufficient to palliate, ameliorate, stabilize, reverse, prevent, slow or delay the progression of the disease state (e.g., cancer). A therapeutically effective amount can be an amount administered in a dosage protocol that includes days or weeks of administration.

In an aspect, the present disclosure provides a method for treating and/or preventing various types of cancer in an individual, the method comprising administering to an individual with cancer, or suspected of being at risk of aquiring cancer, a composition comprising a therapeutically effective amount or a prophylactically effective amount of one or more compounds having the following structure:

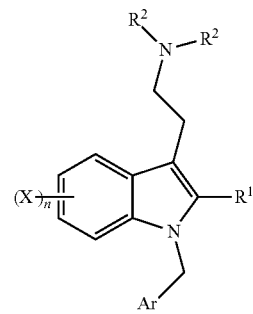

where, Ar is a $C_{5-6}$ aryl; $R^1$ is selected from the group consisting of H, $C_{1-4}$ alkyl, and $C_{5-6}$ aryl; each $R^2$ is independently selected from the group consisting of H, $C_{1-4}$ alkyl, and $C_{5-6}$ aryl; each X, if present, is independently selected from the group consisting of halo, $C_{1-4}$ alkyl, $C_{5-6}$ aryl, and —Y—$R^3$; where Y is selected from the group consisting of —S—, —NH—, —O—; and R³ is H or C₁₋₄ alkyl; and n is 0-4. In an embodiment the patient has colorectal cancer.
The compound may have a formula shown below:
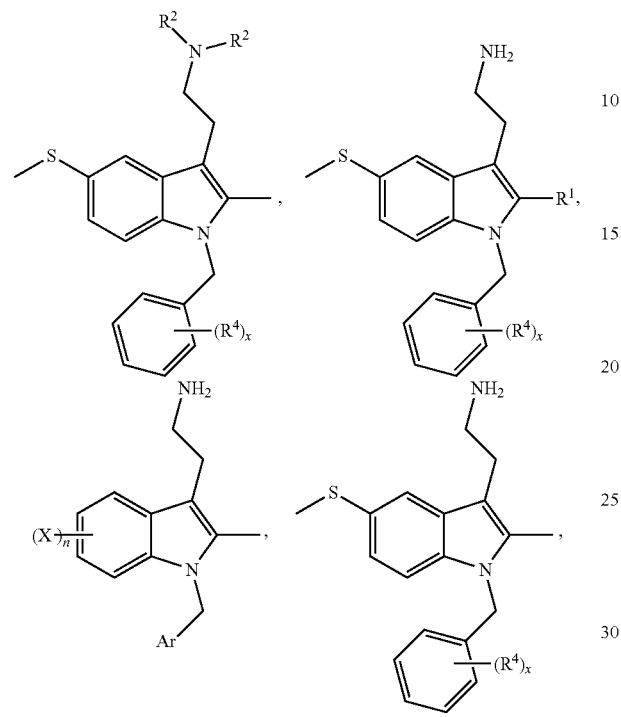
where R⁴ is halo, and x is 0-5.
Further examples of the compounds are shown below:
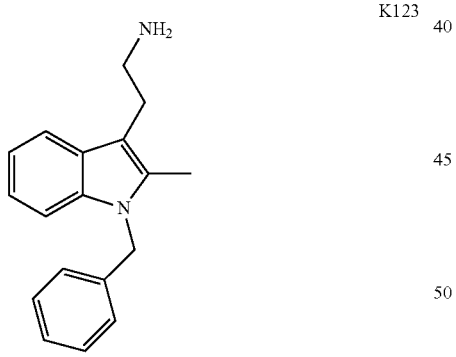
K123
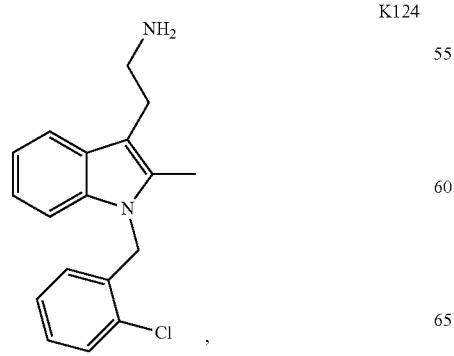
K124
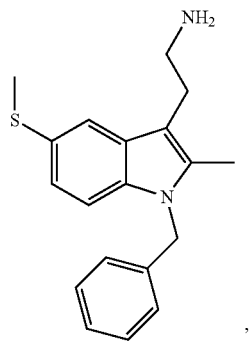
K125
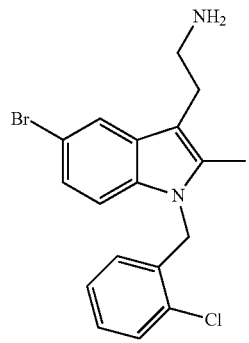
K148
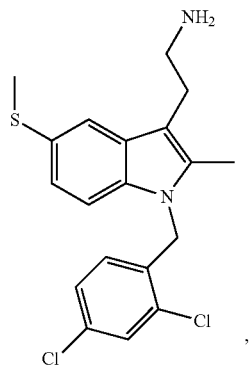
K149
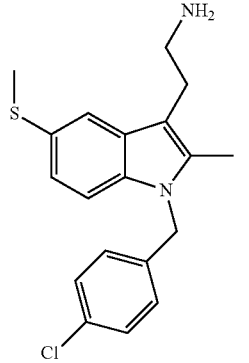
K160

-continued

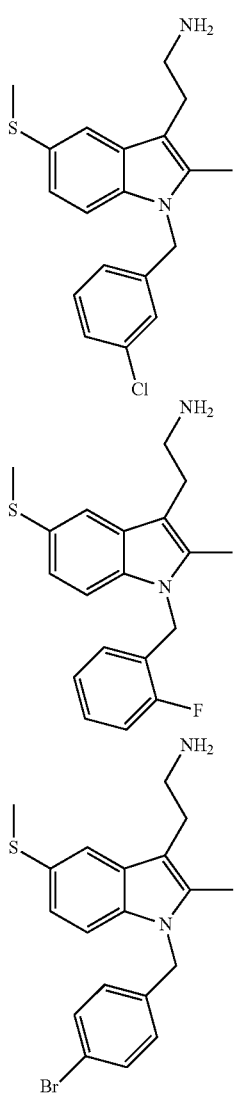

,

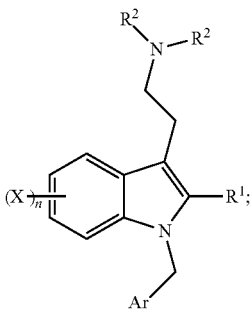

In another aspect, the present disclosure provides a method for inhibiting a SH2-containing inositol 5'-phosphatase (SHIP) in a subject, the method comprising administering to the subject a composition comprising an effective amount of a compound having the following structure:

wherein,
Ar is a $C_{5-6}$ aryl;
$R^1$ is selected from the group consisting of H, $C_{1-4}$ alkyl, and $C_{5-6}$ aryl;

each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;
wherein Y is selected from the group consisting of —S—, —NH—, —O—; and
$R^3$ is H or $C_{1-4}$ alkyl; and n is 0-4, and pharmaceutically acceptable esters, salts, and prodrugs thereof.

In an embodiment, the compound has a formula selected from the group of:

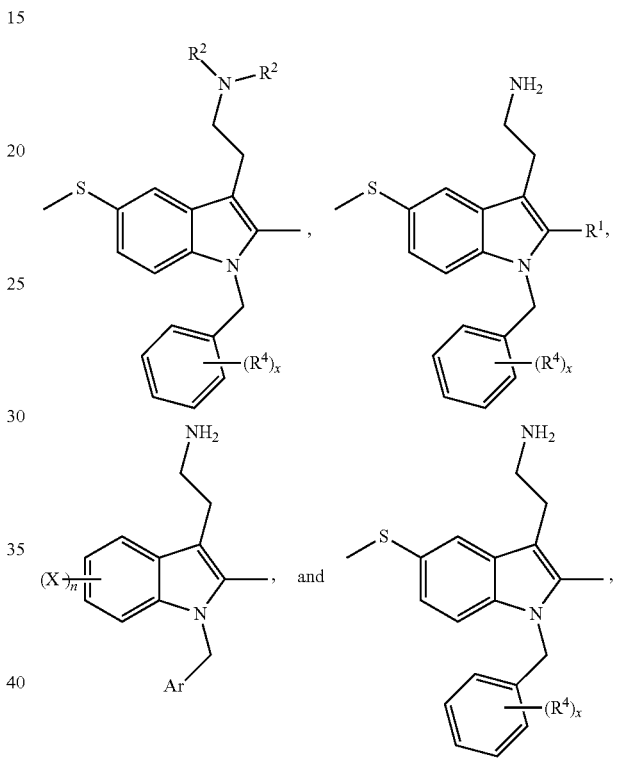

where $R^4$ is halo, and x is 0-5, and pharmaceutically acceptable esters, salts, and prodrugs thereof.

In a further embodiment, the compound has a formula selected from the group of:

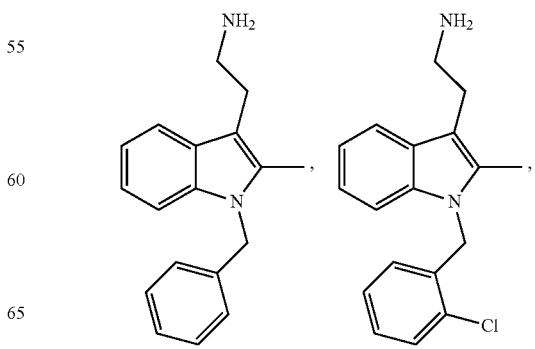

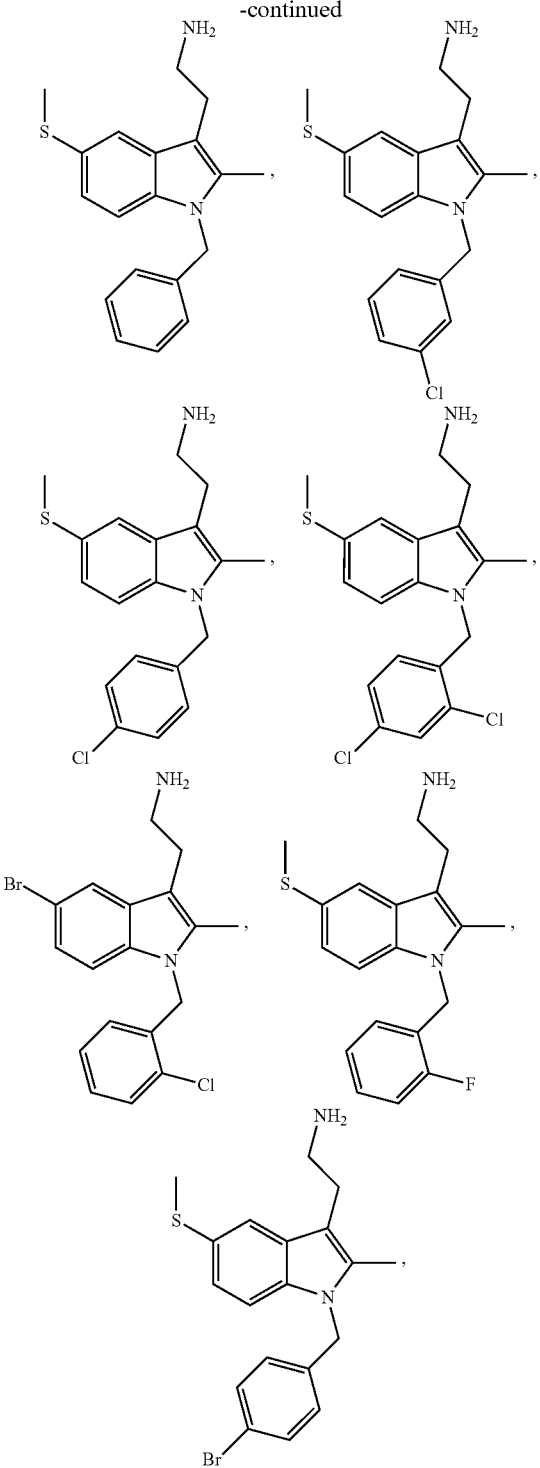

and pharmaceutically acceptable esters, salts, and prodrugs thereof.

In another embodiment, the SHIP is SHIP1. In a further embodiment, the SHIP is SHIP2.

In an embodiment, the compound is a pharmaceutically acceptable ester or salt thereof.

In an embodiment, the compound is 2-(1-benzyl-2-methyl-1H-indol-3-yl)ethan-1-amine, or a pharmaceutically acceptable ester or salt thereof.

In an embodiment, the compound is 2-(1-(2-chlorobenzyl)-2-methyl-1H-indol-3-yl)ethan-1-amine, or a pharmaceutically acceptable ester or salt thereof.

In an embodiment, the compound is 2-(1-benzyl-2-methyl-5-(methylthio)-1H-indol-3-yl)ethan-1-amine, or a pharmaceutically acceptable ester or salt thereof.

In an embodiment, the compound is 2-(5-bromo-1-(2-chlorobenzyl)-2-methyl-1H-indol-3-yl)ethan-1-amine, or a pharmaceutically acceptable ester or salt thereof.

In an embodiment, the compound is 2-(1-(2,4-dichlorobenzyl)-2-methyl-5-(methylthio)-1H-indol-3-yl)ethan-1-amine, or a pharmaceutically acceptable ester or salt thereof.

In an embodiment, the compound is 2-(1-(4-chlorobenzyl)-2-methyl-5-(methylthio)-1H-indol-3-yl)ethan-1-amine, or a pharmaceutically acceptable ester or salt thereof.

In an embodiment, the compound is 2-(1-(3-chlorobenzyl)-2-methyl-5-(methylthio)-1H-indol-3-yl)ethan-1-amine, or a pharmaceutically acceptable ester or salt thereof.

In an embodiment, the compound is 2-(1-(2-fluorobenzyl)-2-methyl-5-(methylthio)-1H-indol-3-yl)ethan-1-amine, or a pharmaceutically acceptable ester or salt thereof.

In an embodiment, the compound is 2-(1-(4-bromobenzyl)-2-methyl-5-(methylthio)-1H-indol-3-yl)ethan-1-amine, or a pharmaceutically acceptable ester or salt thereof.

In an aspect, the present disclosure provides a method for inhibiting a SH2-containing inositol 5'-phosphatase (SHIP) in a subject, wherein the subject has cancer. In an embodiment, the cancer is breast cancer, colorectal cancer, glioblastoma, osteosarcoma, neuroblastoma, lymphoma, multiple myeloma, leukemia, or cancers of epithelial tissue origin. In a particular embodiment, the cancer is breast cancer. In yet another embodiment, the cancer is colorectal cancer.

In another aspect, the present disclosure provides a method for inhibiting a SH2-containing inositol 5'-phosphatase (SHIP) in a subject, wherein the subject is obese, has diabetes or has a metabolic syndrome. In an embodiment, the subject is obese. In another embodiment, the subject has diabetes. In yet another embodiment, the subject has a metabolic syndrome.

In another aspect, the present disclosure provides a composition for use in inhibiting a SH2-containing inositol 5'-phosphatase (SHIP) in a subject, the composition comprising a compound having the following structure:

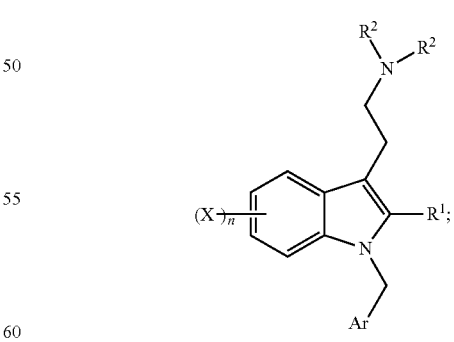

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;

wherein Y is selected from the group consisting of —S—, —NH—, —O—; and $R^3$ is H or $C_{1-4}$ alkyl; and n is 0-4, and pharmaceutically acceptable esters, salts, and prodrugs thereof.

In another embodiment, the compound has a formula selected from:

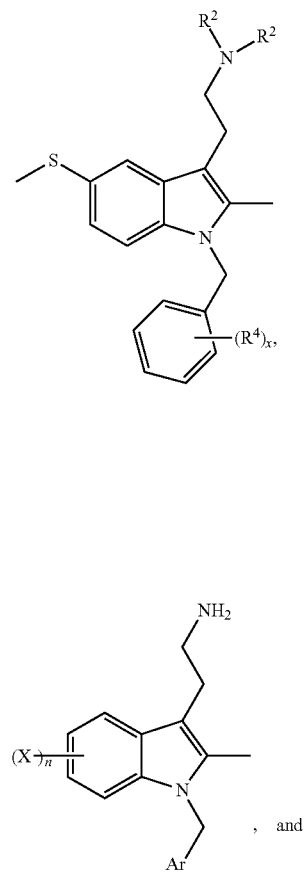

where $R^4$ is halo, and x is 0-5, and pharmaceutically acceptable esters, salts, and prodrugs thereof.

In a further embodiment, the compound has a formula selected from:

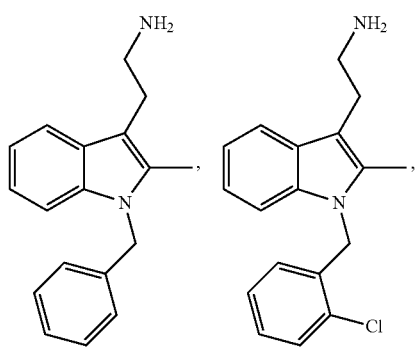

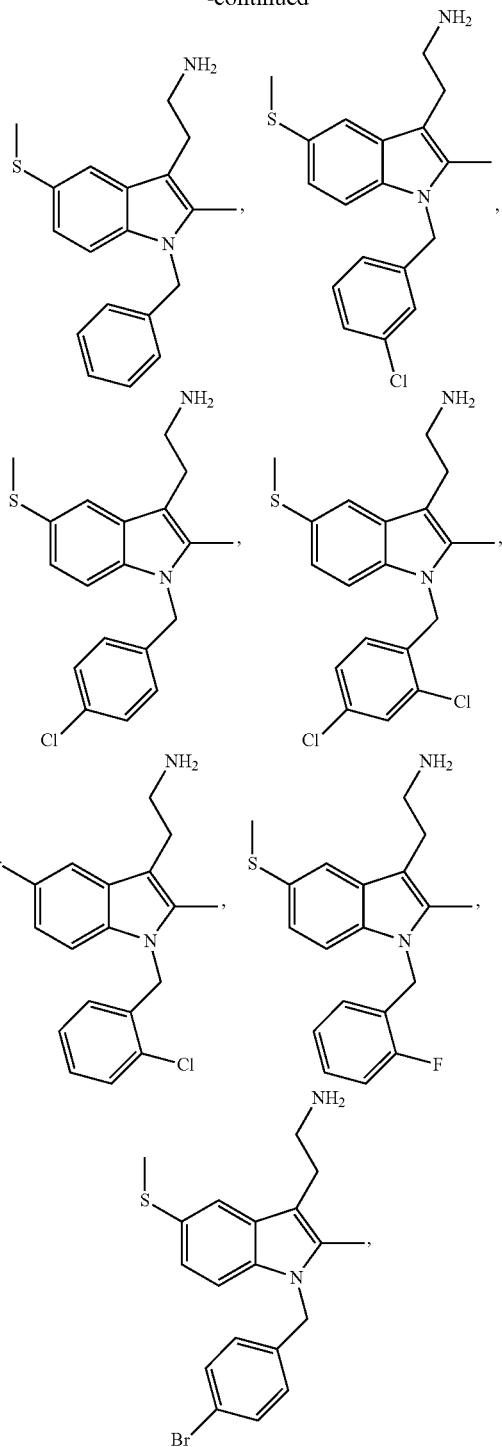

and pharmaceutically acceptable esters, salts, and prodrugs thereof.

In an embodiment, the compound is a pharmaceutically acceptable ester or salt thereof.

In another embodiment, the SHIP activity is SHIP1. In a further embodiment, the SHIP activity is SHIP2.

In an embodiment, the compound is 2-(1-benzyl-2-methyl-1H-indol-3-yl)ethan-1-amine, or a pharmaceutically acceptable ester or salt thereof.

In an embodiment, the compound is 2-(1-(2-chlorobenzyl)-2-methyl-1H-indol-3-yl)ethan-1-amine, or a pharmaceutically acceptable ester or salt thereof.

In an embodiment, the compound is 2-(1-benzyl-2-methyl-5-(methylthio)-1H-indol-3-yl)ethan-1-amine, or a pharmaceutically acceptable ester or salt thereof.

In an embodiment, the compound is 2-(5-bromo-1-(2-chlorobenzyl)-2-methyl-1H-indol-3-yl)ethan-1-amine, or a pharmaceutically acceptable ester or salt thereof.

In an embodiment, the compound is 2-(1-(2,4-dichlorobenzyl)-2-methyl-5-(methylthio)-1H-indol-3-yl)ethan-1-amine, or a pharmaceutically acceptable ester or salt thereof.

In an embodiment, the compound is 2-(1-(4-chlorobenzyl)-2-methyl-5-(methylthio)-1H-indol-3-yl)ethan-1-amine, or a pharmaceutically acceptable ester or salt thereof.

In an embodiment, the compound is 2-(1-(3-chlorobenzyl)-2-methyl-5-(methylthio)-1H-indol-3-yl)ethan-1-amine, or a pharmaceutically acceptable ester or salt thereof.

In an embodiment, the compound is 2-(1-(2-fluorobenzyl)-2-methyl-5-(methylthio)-1H-indol-3-yl)ethan-1-amine, or a pharmaceutically acceptable ester or salt thereof.

In an embodiment, the compound is 2-(1-(4-bromobenzyl)-2-methyl-5-(methylthio)-1H-indol-3-yl)ethan-1-amine, or a pharmaceutically acceptable ester or salt thereof.

In another aspect, the present disclosure provides a composition for inhibiting a SH2-containing inositol 5'-phosphatase (SHIP) in a subject, wherein the subject has cancer. In an embodiment, the cancer is breast cancer, colorectal cancer, glioblastoma, osteosarcoma, neuroblastoma, lymphoma, multiple myeloma, leukemia, or cancers of epithelial tissue origin. In another embodiment, the cancer is breast cancer. In yet another embodiment, the cancer is colorectal cancer.

In another aspect, the present disclosure provides a composition for inhibiting a SH2-containing inositol 5'-phosphatase (SHIP) in a subject, wherein the subject is obese, has diabetes or has a metabolic syndrome. In an embodiment, the subject is obese. In another embodiment, the subject has diabetes. In yet another embodiment, the subject has a metabolic syndrome.

In a further aspect, the present disclosure provides a method for inhibiting a SH2-containing inositol 5'-phosphatase (SHIP) in a mammalian cell, the method comprising administering to the cell a composition comprising an effective amount of a compound having the following structure:

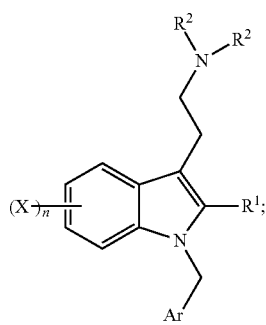

wherein,
Ar is a $C_{5-6}$ aryl;
$R^1$ is selected from the group consisting of H, $C_{1-4}$ alkyl, and $C_{5-6}$ aryl;
each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;

wherein Y is selected from the group consisting of —S—, —NH—, —O—; and
$R^3$ is H or $C_{1-4}$ alkyl; and
n is 0-4, and pharmaceutically acceptable esters, salts, and prodrugs thereof.

In an embodiment, the compound has a formula selected from the group of:

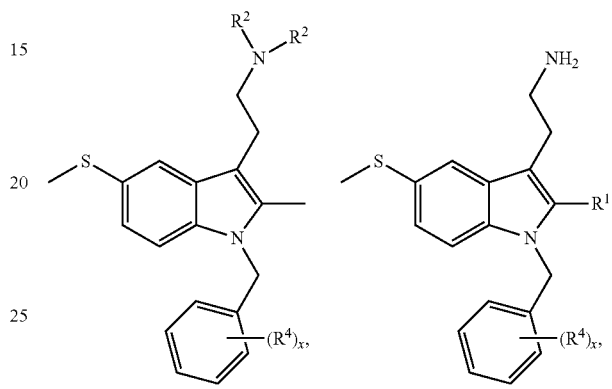

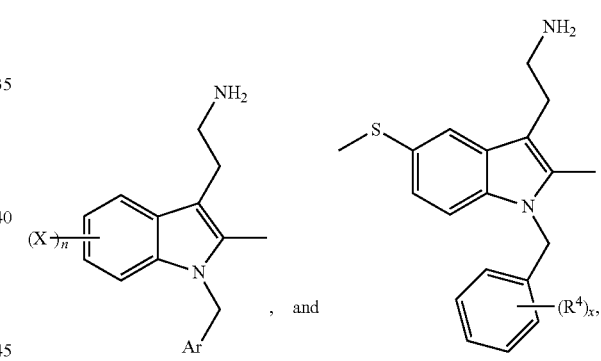

, and where $R^4$ is halo, and x is 0-5, and pharmaceutically acceptable esters, salts, and prodrugs thereof.

In a further embodiment, the compound has a formula selected from the group of:

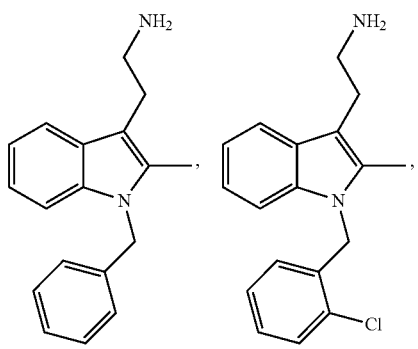

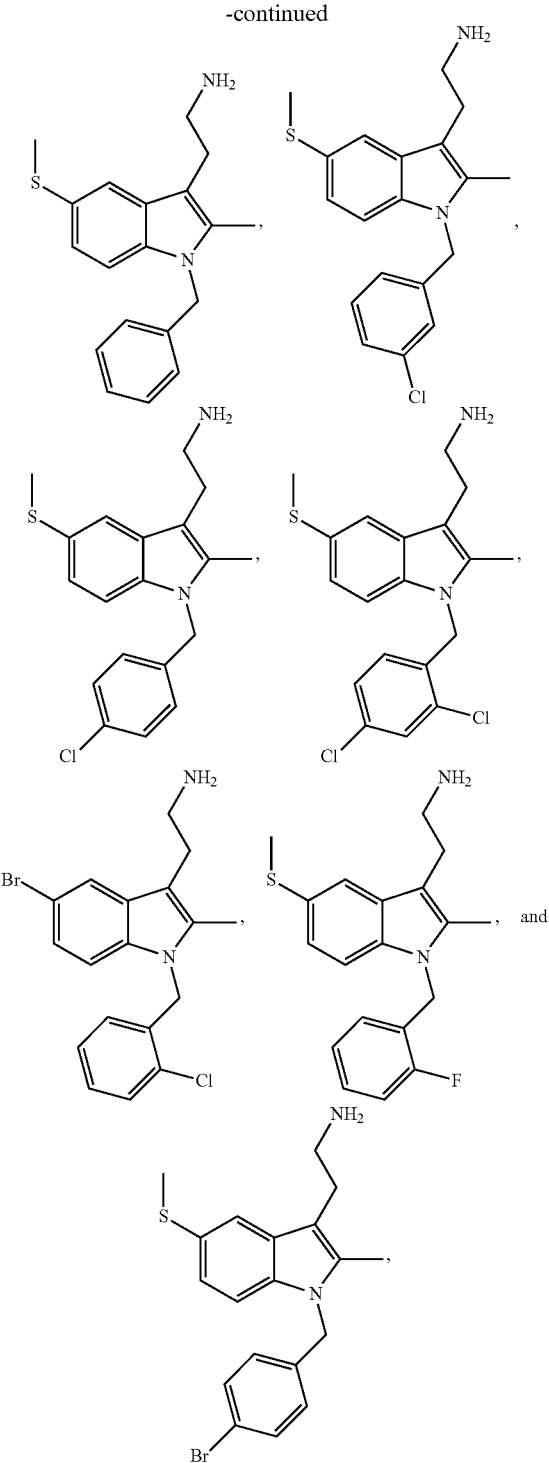

and pharmaceutically acceptable esters, salts, and prodrugs thereof.

In another embodiment, the SHIP is SHIP1. In a further embodiment, the SHIP is SHIP2.

In an embodiment, the compound is a pharmaceutically acceptable ester or salt thereof.

In an embodiment, the mammalian cell is a human cell. In a further embodiment, the human cell is a primary cancer cell. In yet another embodiment, the composition is administered in vivo.

In an embodiment, the compound is 2-(1-benzyl-2-methyl-1H-indol-3-yl)ethan-1-amine, or a pharmaceutically acceptable ester or salt thereof.

In an embodiment, the compound is 2-(1-(2-chlorobenzyl)-2-methyl-1H-indol-3-yl)ethan-1-amine, or a pharmaceutically acceptable ester or salt thereof.

In an embodiment, the compound is 2-(1-benzyl-2-methyl-5-(methylthio)-1H-indol-3-yl)ethan-1-amine, or a pharmaceutically acceptable ester or salt thereof.

In an embodiment, the compound is 2-(5-bromo-1-(2-chlorobenzyl)-2-methyl-1H-indol-3-yl)ethan-1-amine, or a pharmaceutically acceptable ester or salt thereof.

In an embodiment, the compound is 2-(1-(2,4-dichlorobenzyl)-2-methyl-5-(methylthio)-1H-indol-3-yl)ethan-1-amine, or a pharmaceutically acceptable ester or salt thereof.

In an embodiment, the compound is 2-(1-(4-chlorobenzyl)-2-methyl-5-(methylthio)-1H-indol-3-yl)ethan-1-amine, or a pharmaceutically acceptable ester or salt thereof.

In an embodiment, the compound is 2-(1-(3-chlorobenzyl)-2-methyl-5-(methylthio)-1H-indol-3-yl)ethan-1-amine, or a pharmaceutically acceptable ester or salt thereof.

In an embodiment, the compound is 2-(1-(2-fluorobenzyl)-2-methyl-5-(methylthio)-1H-indol-3-yl)ethan-1-amine, or a pharmaceutically acceptable ester or salt thereof.

In an embodiment, the compound is 2-(1-(4-bromobenzyl)-2-methyl-5-(methylthio)-1H-indol-3-yl)ethan-1-amine, or a pharmaceutically acceptable ester or salt thereof.

In a further aspect, the present disclosure provides a composition for use in inhibiting activity associated with SH2-containing inositol 5'-phosphatase (SHIP) in a mammalian cell, the composition comprising a compound having the following structure:

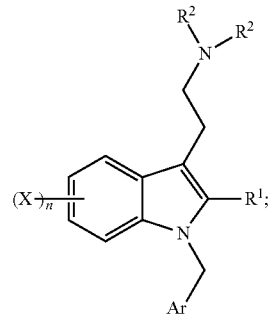

wherein,

Ar is a $C_{5-6}$ aryl;

$R^1$ is selected from the group consisting of H, $C_{1-4}$ alkyl, and $C_{5-6}$ aryl;

each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;

wherein Y is selected from the group consisting of —S—, —NH—, —O—; and $R^3$ is H or $C_{1-4}$ alkyl; and n is 0-4, and pharmaceutically acceptable esters, salts, and prodrugs thereof.

In an embodiment, the compound has a formula selected from:

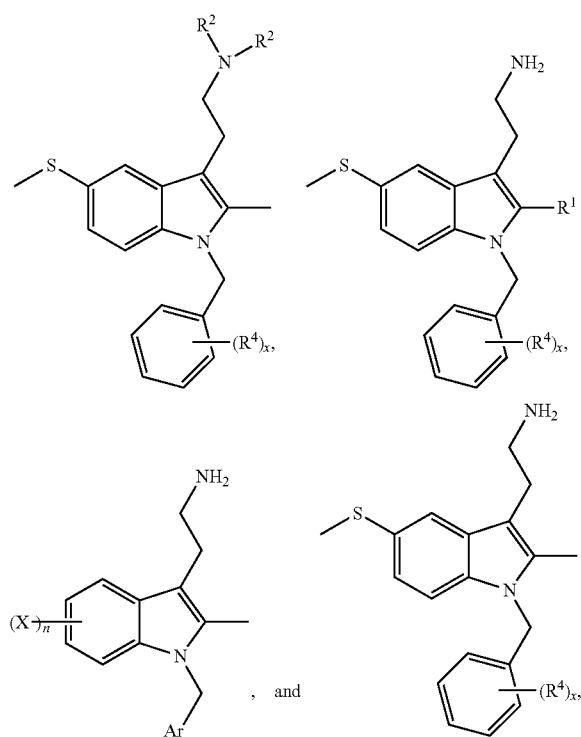

where $R^4$ is halo, and x is 0-5, and pharmaceutically acceptable esters, salts, and prodrugs thereof.

In a further embodiment, the compound has a formula selected from:

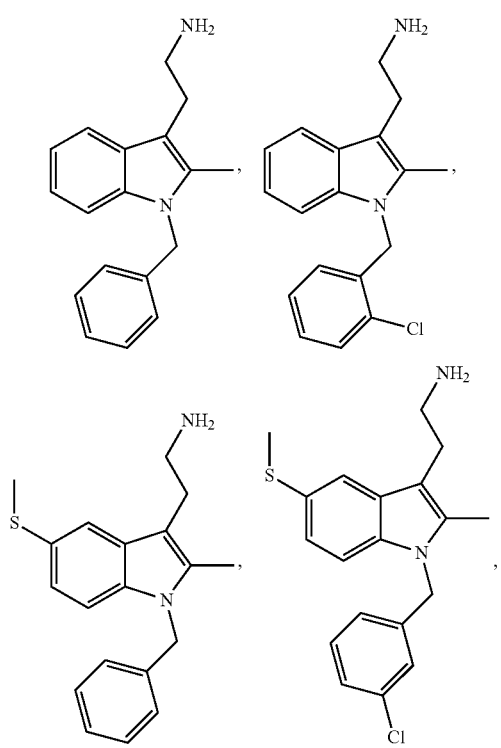

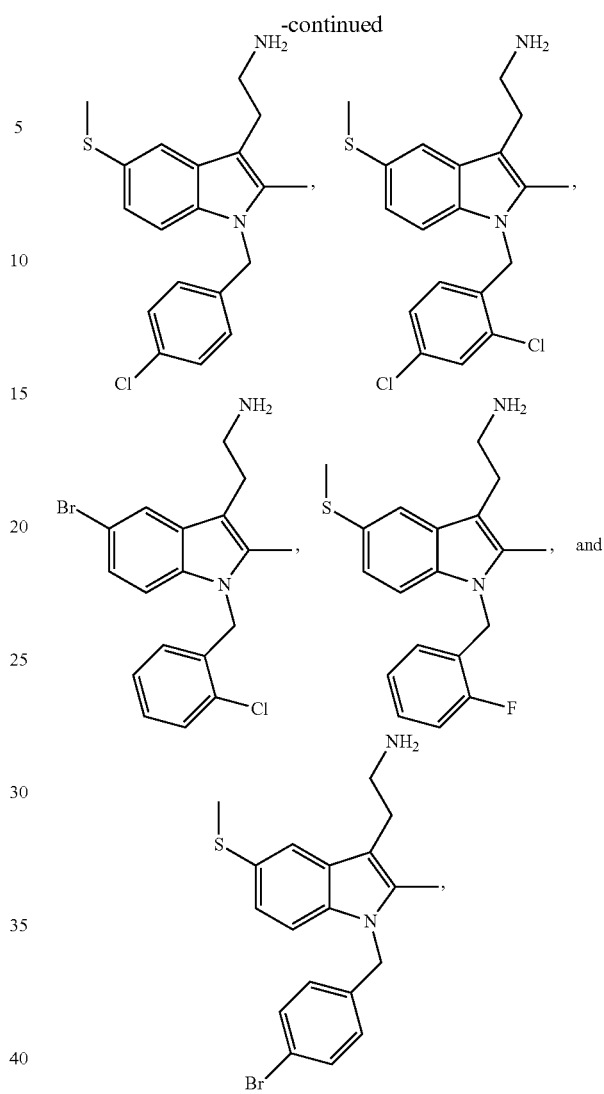

and pharmaceutically acceptable esters, salts, and prodrugs thereof.

In an embodiment, the compound is a pharmaceutically acceptable ester or salt thereof.

In another embodiment, the SHIP is SHIP1. In yet another embodiment, the SHIP is SHIP2.

In a further embodiment, the mammalian cell is a human cell. In a further embodiment, the human cell is a primary cancer cell. In a particular embodiment, the composition is administered in vivo.

In an embodiment, the compound is 2-(1-benzyl-2-methyl-1H-indol-3-yl)ethan-1-amine, or a pharmaceutically acceptable ester or salt thereof.

In an embodiment, the compound is 2-(1-(2-chlorobenzyl)-2-methyl-1H-indol-3-yl)ethan-1-amine, or a pharmaceutically acceptable ester or salt thereof.

In an embodiment, the compound is 2-(1-benzyl-2-methyl-5-(methylthio)-1H-indol-3-yl)ethan-1-amine, or a pharmaceutically acceptable ester or salt thereof.

In an embodiment, the compound is 2-(5-bromo-1-(2-chlorobenzyl)-2-methyl-1H-indol-3-yl)ethan-1-amine, or a pharmaceutically acceptable ester or salt thereof.

In an embodiment, the compound is 2-(1-(2,4-dichlorobenzyl)-2-methyl-5-(methylthio)-1H-indol-3-yl)ethan-1-amine, or a pharmaceutically acceptable ester or salt thereof.

In an embodiment, the compound is 2-(1-(4-chlorobenzyl)-2-methyl-5-(methylthio)-1H-indol-3-yl)ethan-1-amine, or a pharmaceutically acceptable ester or salt thereof.

In an embodiment, the compound is 2-(1-(3-chlorobenzyl)-2-methyl-5-(methylthio)-1H-indol-3-yl)ethan-1-amine, or a pharmaceutically acceptable ester or salt thereof.

In an embodiment, the compound is 2-(1-(2-fluorobenzyl)-2-methyl-5-(methylthio)-1H-indol-3-yl)ethan-1-amine, or a pharmaceutically acceptable ester or salt thereof.

In an embodiment, the compound is 2-(1-(4-bromobenzyl)-2-methyl-5-(methylthio)-1H-indol-3-yl)ethan-1-amine, or a pharmaceutically acceptable ester or salt thereof.

In an aspect, the present disclosure provides a pharmaceutical composition comprising an effective amount of a compound having the following structure:

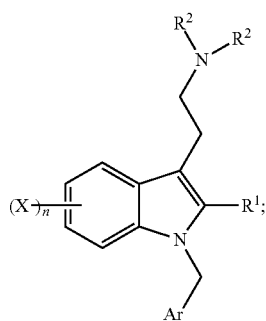

wherein,

Ar is a $C_{5-6}$ aryl;

$R^1$ is selected from the group consisting of H, $C_{1-4}$ alkyl, and $C_{5-6}$ aryl;

each $R^2$ is independently selected from the group consisting of H, $C_{1-4}$ alkyl, and $C_{5-6}$ aryl;

each X, if present, is independently selected from the group consisting of halo, $C_{1-4}$ alkyl, $C_{5-6}$ aryl, and —Y—$R^3$;

wherein Y is selected from the group consisting of —S—, —NH—, —O—; and $R^3$ is H or $C_{1-4}$ alkyl; and n is 0-4, and pharmaceutically acceptable esters, salts, and prodrugs thereof.

In an embodiment, the compound has a formula selected from:

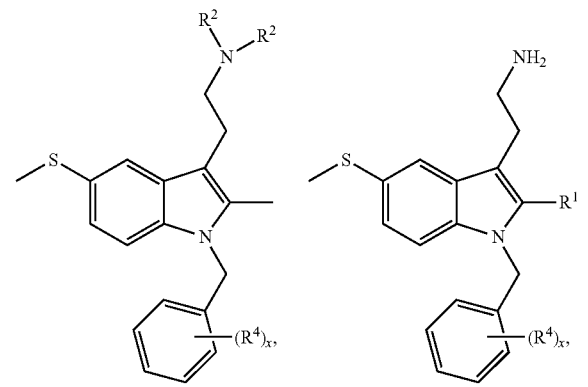

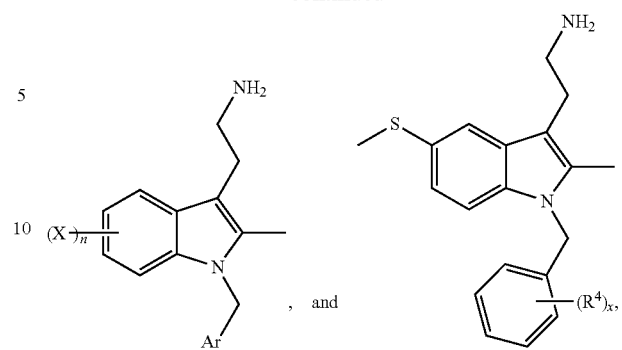

where $R^4$ is halo, and x is 0-5, and pharmaceutically acceptable esters, salts, and prodrugs thereof.

In a further embodiment, the compound has a formula selected from:

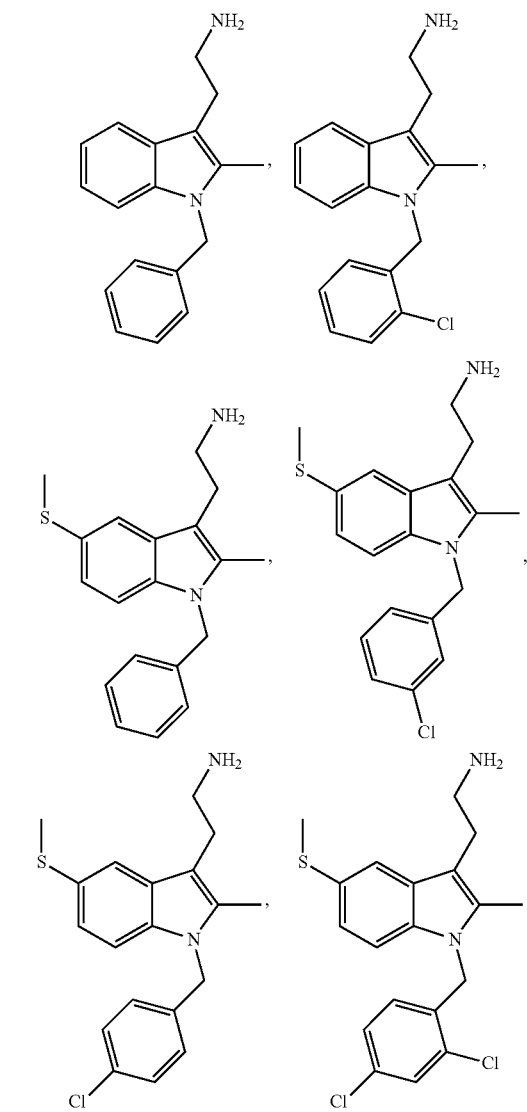

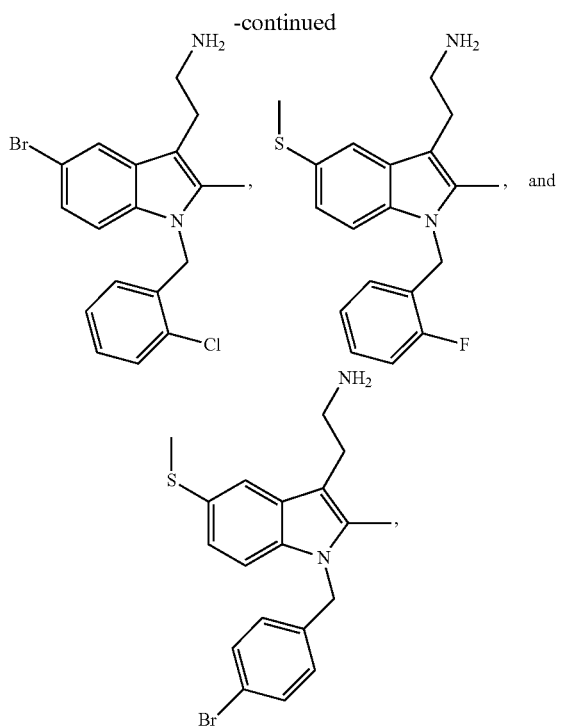

and pharmaceutically acceptable esters, salts, and prodrugs thereof.

In an embodiment, the compound is a pharmaceutically acceptable ester or salt thereof.

In an embodiment, the compound is 2-(1-benzyl-2-methyl-1H-indol-3-yl)ethan-1-amine, or a pharmaceutically acceptable ester or salt thereof.

In an embodiment, the compound is 2-(1-(2-chlorobenzyl)-2-methyl-1H-indol-3-yl)ethan-1-amine, or a pharmaceutically acceptable ester or salt thereof.

In an embodiment, the compound is 2-(1-benzyl-2-methyl-5-(methylthio)-1H-indol-3-yl)ethan-1-amine, or a pharmaceutically acceptable ester or salt thereof.

In an embodiment, the compound is 2-(5-bromo-1-(2-chlorobenzyl)-2-methyl-1H-indol-3-yl)ethan-1-amine, or a pharmaceutically acceptable ester or salt thereof.

In an embodiment, the compound is 2-(1-(2,4-dichlorobenzyl)-2-methyl-5-(methylthio)-1H-indol-3-yl)ethan-1-amine, or a pharmaceutically acceptable ester or salt thereof.

In an embodiment, the compound is 2-(1-(4-chlorobenzyl)-2-methyl-5-(methylthio)-1H-indol-3-yl)ethan-1-amine, or a pharmaceutically acceptable ester or salt thereof.

In an embodiment, the compound is 2-(1-(3-chlorobenzyl)-2-methyl-5-(methylthio)-1H-indol-3-yl)ethan-1-amine, or a pharmaceutically acceptable ester or salt thereof.

In an embodiment, the compound is 2-(1-(2-fluorobenzyl)-2-methyl-5-(methylthio)-1H-indol-3-yl)ethan-1-amine, or a pharmaceutically acceptable ester or salt thereof.

In an embodiment, the compound is 2-(1-(4-bromobenzyl)-2-methyl-5-(methylthio)-1H-indol-3-yl)ethan-1-amine, or a pharmaceutically acceptable ester or salt thereof.

In an aspect, the present disclosure provides a method for inhibiting SHIP2 and/or SHIP1 in an individual, the method comprising administering to the individual a composition comprising a therapeutically effective amount of a compound of the present disclosure. Compositions of the present disclosure can be used to treat various cancers, such as, for example, colorectal cancer and breast cancer, glioblastoma, osteosarcoma and neuroblastoma, lymphoma, multiple myeloma, leukemia, or other cancers of the epithelial tissue origin. The compositions may comprise one or more of the compounds described herein. For example, the compositions may comprise one or more of K123, K124, K125, K148, K149, and K160.

The present compositions may also be used to treat obesity or reduce body fat in an individual. The method involves administering a SHIP 2 inhibitor of the present disclosure to a subject in an amount effective to treat obesity and/or reduce body fat in said subject.

In another aspect, the present disclosure relates to a method to treat or prevent diabetes in a subject. This method involves administering a compound of the present disclosure to a subject in an amount effective to treat or prevent diabetes in the subject.

In another aspect, the present disclosure relates to a method to reduce glucose intolerance or insulin resistance in a subject. This method involves administering a compound of the present disclosure to a subject in an amount effective to reduce glucose intolerance or insulin resistance the subject.

In one aspect, the disclosure provides a kit for treating cancer in an individual. The kit comprises a compound of the present disclosure, pharmaceutically acceptable esters, salts, and prodrugs thereof, and instructions for use. The instructions may include details on one or more of the following: dosage, frequency, number of administrations to be carried out (such as number of tablets to be consumed), whether the composition needs to be taken with food, water etc., storage of the composition, and the like.

Compounds of the disclosure can exist as salts. Pharmaceutically acceptable salts of the compounds of the disclosure generally are preferred in the methods of the disclosure. As used herein, the term "pharmaceutically acceptable salts" refers to salts or zwitterionic forms of a compound of the present disclosure. Salts of compounds of the present disclosure can be prepared during the final isolation and purification of the compounds or separately by reacting the compound with an acid having a suitable cation. The pharmaceutically acceptable salts of a compound of the present disclosure are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quatemized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include a compound of the present disclosure as well as pharmaceutically acceptable salts, hydrates, or prodrugs thereof.

Prodrugs of a compound of the present disclosure also can be used as the compound in a method of the present disclosure. Compounds of the present disclosure can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compositions comprising a compound of the disclosure and a pharmaceutical agent can be prepared at a patient's bedside, or by a pharmaceutical manufacture. In the latter case, the compositions can be provided in any suitable container, such as a sealed sterile vial or ampoule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described herein can include one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

The amount of provided compounds that may be combined with carrier materials to produce a composition in a single dosage form will vary depending upon the patient to be treated and the particular mode of administration. The compositions may be formulated such that a desired dosage of the inhibitor can be administered to a patient receiving these compositions.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. The compositions can be used in conjunction with any other conventional treatment modality designed to improve the disorder for which a desired therapeutic or prophylactic effect is intended, non-limiting examples of which include surgical interventions and radiation therapies. The compositions can be administered once, or over a series of administrations at various intervals determined using ordinary skill in the art, and given the benefit of the present disclosure.

The pharmaceutical compositions may be provided in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

Identifying an individual in need of treatment can be in the judgment of a health care professional and can be subjective (e.g. opinion) or objective (e.g. measurable by a test or diagnostic method). In other methods, the individual is prescreened or identified as in need of such treatment by assessment for a relevant marker or indicator of suitability for such treatment.

For human use, a compound of the present disclosure can be administered alone, but generally is administered in admixture with a pharmaceutical carrier selected with regard to the intended route of administration and standard pharmaceutical practice. Pharmaceutical compositions for use in accordance with the present disclosure can be formulated in a conventional manner using one or more physiologically acceptable carrier comprising excipients and auxiliaries that facilitate processing of a compound of the present disclosure into pharmaceutical preparations.

For veterinary use, a compound of the present disclosure, or a pharmaceutically acceptable salt or prodrug, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, bovines or ungulates.

The present compounds may be used with pharmaceutically acceptable carriers, which may be solvents, suspending agents, vehicles or the like for delivery to humans or animals. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Examples of pharmaceutically-acceptable carriers include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The present compositions may be administered by any suitable route—either alone or as in combination with other therapeutic or non-therapeutic agents. Administration can be accomplished by any means, such as, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth.

When administered in combination with other therapeutics, a present compound may be administered at relatively lower dosages. In addition, the use of targeting agents may allow the necessary dosage to be relatively low. Certain compounds may be administered at relatively high dosages due to factors including, but not limited to, low toxicity and high clearance.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the specification may be read as if prefaced by the word "about" even though the term "about" may not expressly appear with the value, amount or range. Numerical parameter should be construed in light of the number of reported significant digits and by applying ordinary rounding techniques.

The steps of the methods described in the various embodiments and examples disclosed herein are sufficient to inhibit the growth of cancer cells in an individual in need of treatment. Thus, in an embodiment, a method consists essentially of a combination of the steps of the methods disclosed herein. In another embodiment, the method consists of such steps.

When used for treatment of obesity, treatment of diabetes or glucose intolerance, the steps of the method disclosed herein are sufficient to provide the intended effect. Thus, in one embodiment, the present method consists essentially of, or consists of the steps provided herein.

EXAMPLES

The following examples are presented to illustrate the present disclosure. They are not intended to be limiting in any manner.

Example 1

This example describes the synthesis of some compounds of the present disclosure.

Materials and Methods

Figure 6:
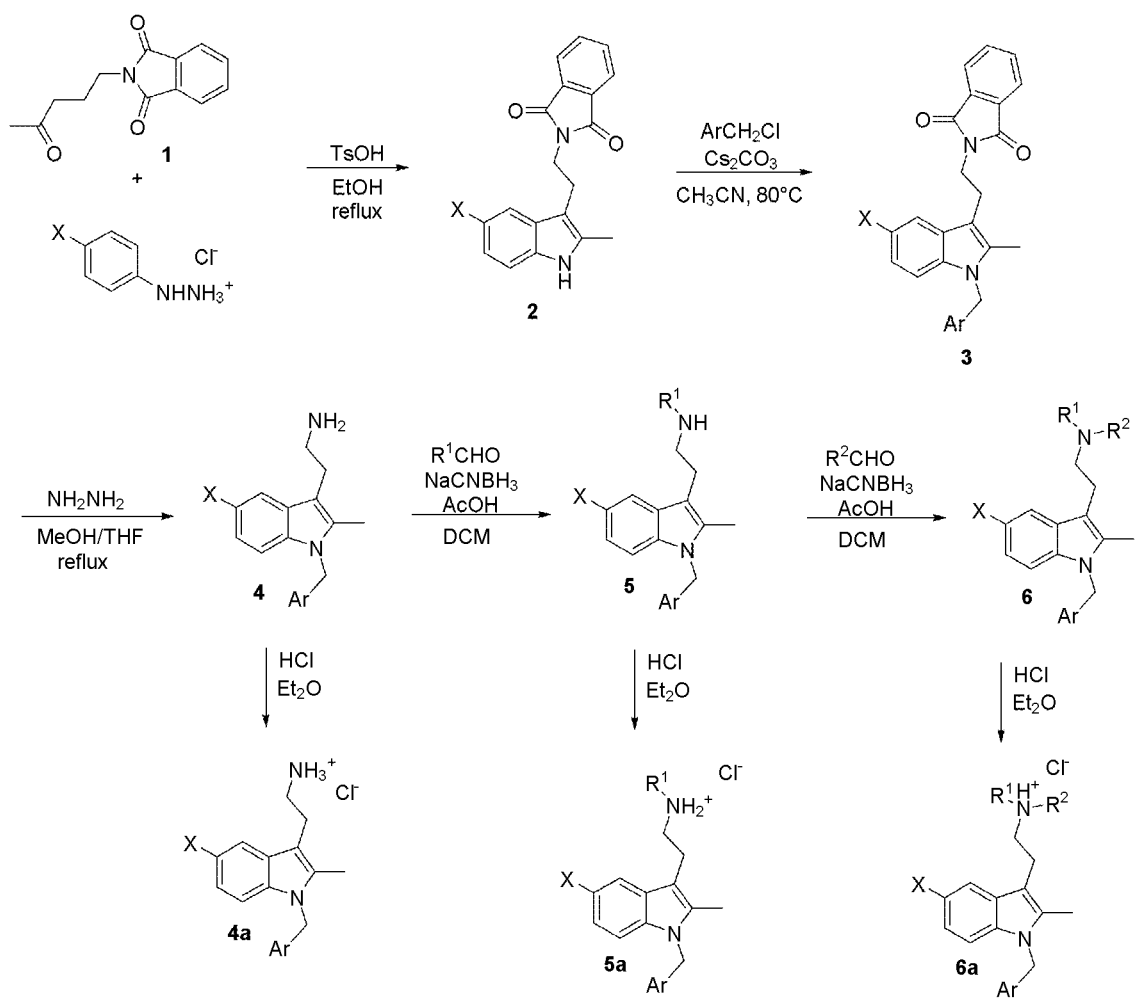
FIG. 6. is a schematic of the general synthesis of Tryptamine SHIP inhibitors.
Figure 8A:
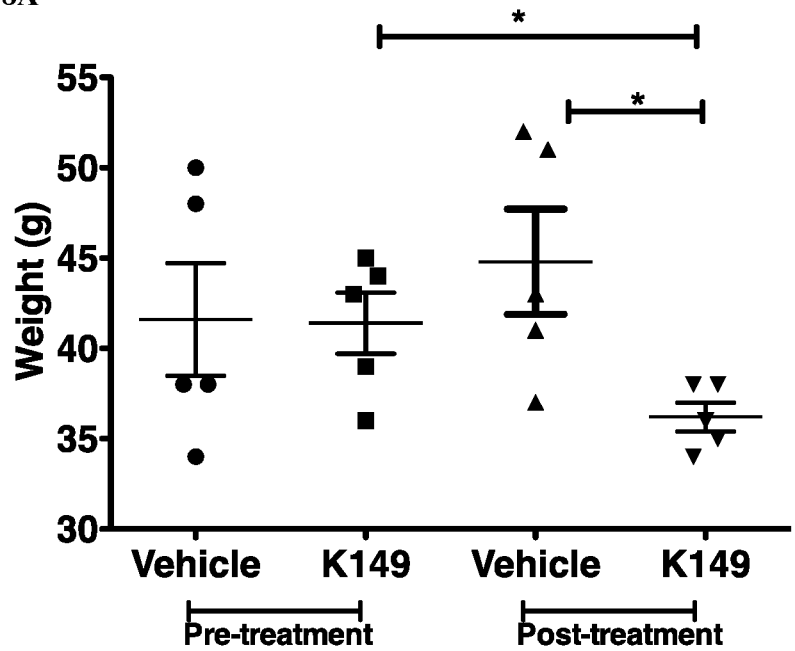
FIGS. 8A-B are graphs showing the effect of K149 on obesity. Mice were maintained on a high fat diet (HFD) prior to treatment with K149 and then treated with K149 (2× week, i.p., 10 mg/kg) for two weeks while continuing to consume a HFD. Their weight was measured at the end of the two week treatment period and both total weight (FIG. 8A) and % body weight (FIG. 8B) of the K149 mice showed significant reductions despite continued consumption of a HFD. (*p<0.05, ***p<0.001) The K149 mice showed reduced body weight vs. vehicle mice weighed after the 2 week treatment and vs. their own weight as measured prior to K149 treatment.
Figure 8B:
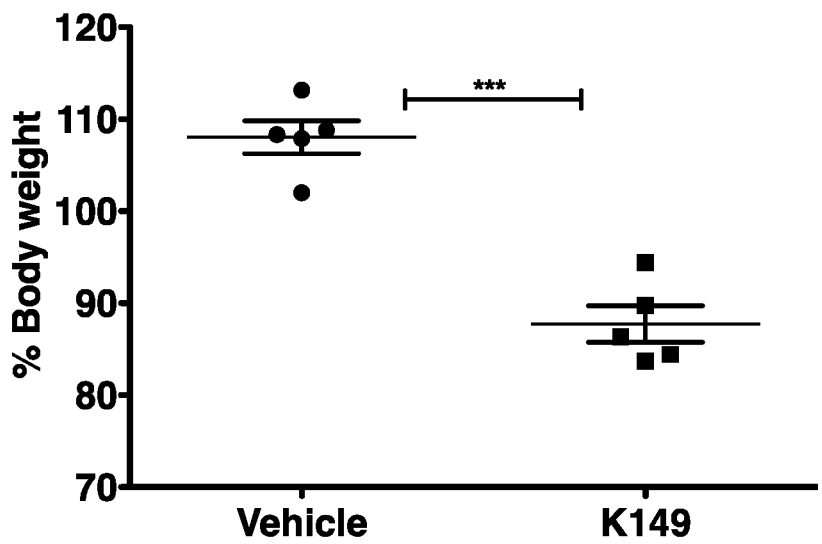
Figure 9A:
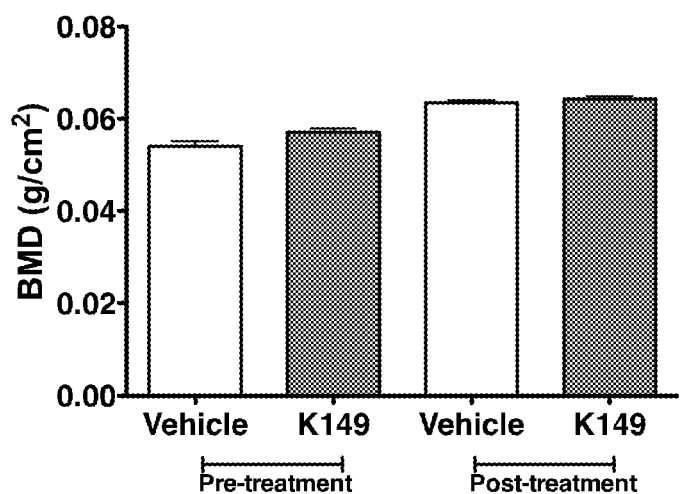
FIGS. 9A-B are bar graphs depicting the effect of K149 on bone mineral density (FIG. 9A) and bone mineral content (FIG. 9B) in mice on a high fat diet.
Figure 9B:
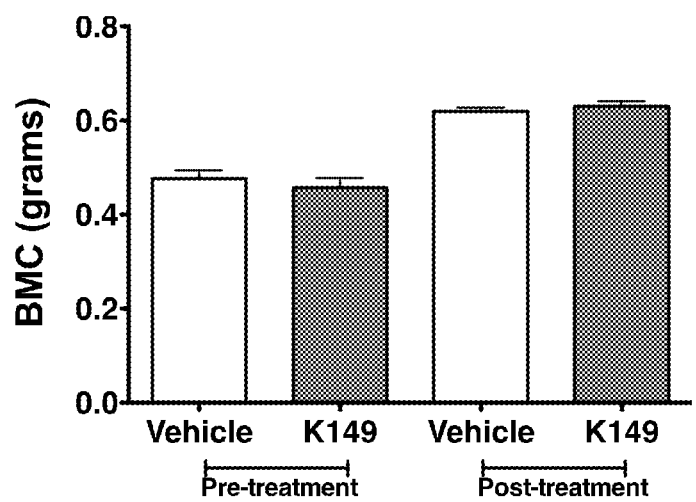

General Method for preparation of Compound 2: (FIG. 6).
Corresponding phenyl hydrazine (1 eq, 1.52 mmol) and ketone 1 (0.9 eq, 1.36 mmol) were dissolved in 5 mL of ethanol. TsOH.H$_2$O (4 eq, 6.08 mmol) was added. The reaction mixture was heated to reflux for approximately 18 h. The reaction mixture was then cooled to room temperature and poured into 30 mL of 1M NaOH. The mixture was then extracted with dichloromethane (3×20 mL). The organic extracts were dried over Na$_2$SO$_4$, filtered and concentrated to afford Compound 2. These compounds were purified using mixtures of ethyl acetate in hexanes. The stated TLC solvent system is used for purifying the indoles.

General Procedure for preparation of Compound 3 (FIG. 6). The corresponding Compound 2 (1 eq, 0.33 mmol) was dissolved in 6 mL acetonitrile. Cesium carbonate (6 eq, 1.98 mmol) was added and the mixture was heated to 80° C. The corresponding benzyl halide was then added. The reaction mixture was maintained at 80° C. for 18 h. The reaction was quenched with water (10 mL), the organic layer separated, and the aqueous layer extracted with ethyl acetate (3×10 mL). The combined organic extracts were dried with Na$_2$SO$_4$, filtered, and concentrated. Purification by silica gel chromatography afforded Compound 3. The stated TLC solvent system is used for purifying the indoles.

General Method for preparation of Compound 4 (FIG. 6). Compound 3 (1 eq, 0.38 mmol) was dissolved in 5 mL methanol. Hydrazine hydrate (85%, 5 eq, 1.90 mmol) was added. The reaction mixture is refluxed for 0.5 h. The reaction mixture was cooled and concentrated. The resulting residue was dissolved in dichloromethane and purified by silica gel chromatography (90% dichloromethane: 9% methanol: 1% ammonium hydroxide) to afford Compound 4.

General Method for preparation of compounds 4a, 5a, and 6a (FIG. 6). The corresponding compound (1 eq, 0.40 mmol) was dissolved in 1 mL of ether. HCl. Et$_2$O (10 eq, 4.0 mmol) was added. The reaction mixture was allowed to stand for 20 minutes and then concentrated. Recrystallization from mixtures of ether, hexanes or methanol afforded the corresponding HCl salt.

Examples

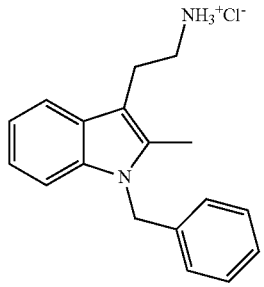

K123

2-[1-benzyl-2-methyl-5-1H-3-yl] ethanaminium chloride. Obtained as white solid. mp=158-161° C. (50% ether in hexanes). IR (thin film) 3420, 2917, 2942, 2890, 1554, 1375, 1238 cm$^{-1}$; $^1$H NMR (300 MHz, CDCl$_3$) δ 7.78 (s, 1H), 7.62 (s, 1H), 7.47 (s, 1H), 7.17 (t, J=6.0 Hz, 1H), 6.98 (d, J=6.0 Hz, 1H), 6.13 (d, J=6.0 Hz), 2.89 (bs, 4H), 2.24 (s, 3H), 2.19 (s, 3H). $^{13}$C NMR (75 MHz, DMSO-d$_6$) δ 139.1, 136.8, 134.8, 134.6, 129.2, 127.8, 127.7, 126.9, 121.3, 119.6, 118.6, 110.3, 106.7, 46.3, 33.5, 10.6.

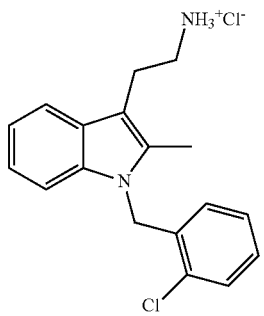

K124

2-[1-(2-chlorobenzyl)-2-methyl-5-1H-3-yl] ethanaminium chloride. 29a. Obtained as a yellow solid. mp=161-169° C. (methanol). IR (thin film) 3466, 2988 2942, 2910, 1561, 1448, 1375, 1242, 939 cm$^{-1}$; $^1$H NMR (300 MHz, CDCl$_3$) δ 7.43-7.41 (m, 1H), 7.39-7.31 (m, 1H), 7.29-7.27 (m, 2H), 7.21-7.15 (m, 2H), 7.05-7.02 (m, 1H), 6.93-6.85 (m, 1H), 5.28 (s, 2H), 3.36 (bs, 2H), 2.87-2.83 (m, 4H), 2.21 (s, 3H). $^{13}$C NMR (75 MHz, DMSO-d$_6$) δ 136.7, 136.0, 134.8, 131.8, 130.1, 128.3, 127.9, 127.5, 121.6, 119.8, 118.3, 110.0, 107.2, 44.5, 38.0, 22.7, 10.4.

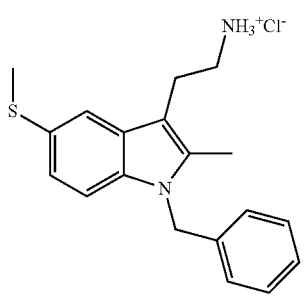

K125

2-[1-benzyl-2-methyl-5-(methylmercapto)-1H-3-yl] ethanaminium chloride. Obtained as a white solid. mp=178-189° C. (40% ether in hexanes). IR (thin film) 3001, 2990, 1716, 1650, 1363, 1222, 1093, 760 cm$^{-1}$; $^1$H NMR (300 MHz, CDCl$_3$) δ 7.73-7.72 (m, 2H), 7.62-7.59 (m, 2H), 7.56 (s, 1H), 7.43-7.40 (dd, J=6.0, 2.0 Hz, 1H), 7.33-7.28 (m, 1H), 7.24-7.21 (m, 1H), 7.14-7.10 (m, 2H), 7.02-6.95 (m, 2H), 4.72 (s, 2H) 3.94-3.83 (m, 2H), 3.09-3.04 (m, 2H), 2.54 (s, 3H) 2.32 (s, 3H). $^{13}$C NMR (75 MHz, DMSO-d$_6$) δ 138.9, 136.0, 135.8, 135.7, 135.4, 129.5, 127.7, 127.9, 127.5, 121.6, 119.8, 118.3, 110.0, 107.2, 44.5, 38.0, 22.7, 10.4.

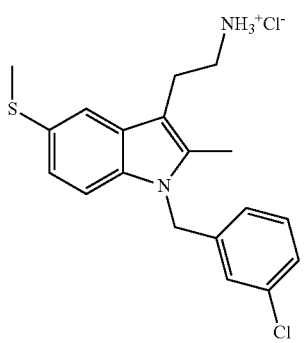

2-[1-(3-chlorobenzyl)-2-methyl-5-(methylmercapto)-1H-3-yl] ethanaminium chloride. Obtained as a black oil. TLC R$_f$=0.50 (90% dichloromethane: 9% methanol: 1% ammonium hydroxide). mp=198-203° C. IR (thin film) 3430, 2910, 2790, 1543, 1375, 824 cm$^{-1}$; $^{13}$C NMR (75 MHz, DMSO-d$_6$) δ 9.05 (s. 3H), 7.50 (s, 1H), 7.14 (d, J=6.0 Hz, 1H), 7.29 (m, 1H), 6.93 (m, 1H), 6.13 (d, J=6.0 Hz), 3.02-2.93 (m, 4H), 2.39 (bs, 3H), 2.24 (s, 3H).

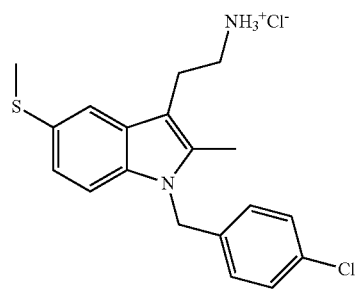

K160

2-[1-(4-chlorobenzyl)-2-methyl-5-(methylmercapto)-1H-3-yl] ethanaminium chloride. Obtained as brown solid. mp=198-209° C. (methanol). IR (thin film) 3433, 2997, 2912, 2890, 1554, 1375, 1238 cm$^{-1}$; $^1$H NMR (300 MHz, CDCl$_3$) δ 7.78 (s, 3H), 7.62 (s, 1H), 7.47 (s, 1H), 7.17 (t, J=6.0 Hz, 1H), 6.98 (d, J=6.0 Hz, 1H), 6.13 (d, J=6.0 Hz), 2.89 (bs, 4H), 2.24 (s, 3H), 2.19 (s, 3H). $^{13}$C NMR (75 MHz, DMSO-d$_6$): δ 136.4, 135.4, 134.5, 133.3, 129.2, 129.0, 127.5, 123.3, 119.3, 109.8, 108.9, 46.3, 42.0, 27.9, 19.1, 10.6.

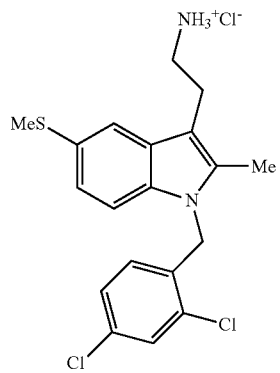

K149

2-[1-(2,4-dichlorobenzyl)-2-methyl-5-(methylmercapto)-1H-3-yl] ethanaminium chloride. Obtained as white powder. mp=231-233° C. (methanol). $^1$H NMR (400 MHz, DMSO-d6) δ 7.84 (br s, 3H), 7.70 (d, J=2.4 Hz, 1H), 7.57 (s, 1H), 7.28-7.24 (m, 2H), 7.06 (dd, J=8.4, 1.2 Hz, 1H), 6.19 (d, J=8.4 Hz, 1H), 5.41 (s, 2H), 2.99-2.94 (m, 4H), 2.49 (s, 3H), 2.25 (s, 3H).

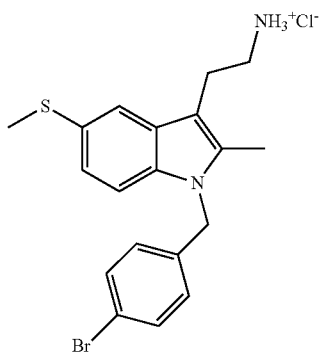

2-[1-(4-bromobenzyl)-2-methyl-5-(methylmercapto)-1H-3-yl] ethanaminium chloride. Obtained as yellow oil. IR (thin film) 3225, 2879, 2850, 1550, 1345, 1224 cm$^{-1}$; $^1$H NMR (300 MHz, CDCl$_3$) δ 7.78 (s, 3H), 7.62 (s, 1H), 7.47 (s, 1H), 7.17 (t, J=6.0 Hz, 1H), 6.98 (d, J=6.0 Hz, 1H), 6.13 (d, J=6.0 Hz), 2.89 (bs, 4H), 2.24 (s, 3H), 2.19 (s, 3H). $^{13}$C NMR (75 MHz, DMSO-d$_6$): δ 135.4, 133.7, 132.6, 131.6, 131.3, 129.0, 127.9, 119.3, 111.8, 111.3, 108.0, 53.0, 40.3, 23.5, 14.1, 10.6.

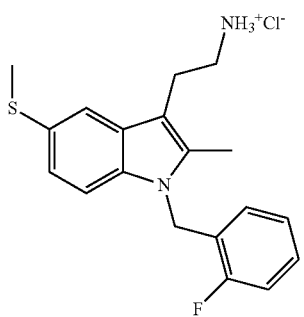

2-[1-(2-fluorobenzyl)-2-methyl-5-(methylmercapto)-1H-3-yl] ethanaminium chloride. 29g. Obtained as brown oil. IR (thin film) 3446, 2917, 2942, 2980, 1554, 1375, 1238, 764 cm$^{-1}$; $^1$H NMR (300 MHz, CDCl$_3$) δ 7.50 (s, 3H), 7.47-6.96 (m, 4H), 7.86-6.79 (m, 2H), 6.31 (t, J=6.0 Hz, 1H), 5.19 (s, 2H), 2.86 (bs, 4H), 2.40 (s, 3H), 2.12 (s, 3H). $^{13}$C NMR (75 MHz, DMSO-d$_6$) δ 135.6, 135.4, 129.5, 128.4, 128.1, 127.3, 124.8, 124.3, 123.8, 123.3, 118.6, 110.0, 106.2, 105.9, 46.3, 42.0, 27.9, 19.1, 10.6.

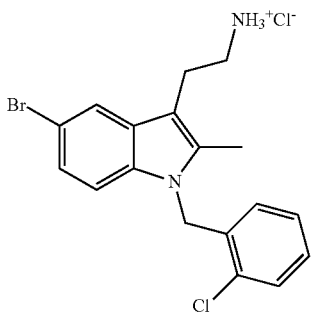

2-[1-(2-chlorobenzyl)-2-methyl-5-(bromo)-1H-3-yl] ethanaminium chloride. Obtained as pale yellow oil. IR (thin film) 3446, 2917, 2942, 2980, 1554, 1375, 1238, 764 cm$^{-1}$; $^1$H NMR (300 MHz, CDCl$_3$) δ 7.60 (s, 3H), 7.29 (d, J=9.0 Hz, 1H), 7.07-7.01 (m, 2H), 6.89-6.84, 6.80 (d, J=9.0 Hz, 1H), 6.01 (d, J=9.0 Hz, 1H), 5.19 (s, 2H), 3.04 (bs, 2H), 2.96 (bs, 2H), 2.12 (s, 3H), $^{13}$C NMR (75 MHz, DMSO-d$_6$): 135.5, 135.2, 134.9, 132.0, 129.8, 129.6, 128.8, 127.5, 126.9, 128.8, 127.6, 126.8, 124.1, 120.8, 113.0, 110.7, 108.1, 44.6, 41.6, 29.9, 10.3.

Example 2

This example describes K149 as a SHIP inhibitor and its activity against a variety of cancer cell lines.

Materials and Methods

Cell lines. MM cell line OPM2 (ATCC, Rockville, Md.) was routinely maintained in IMDM (ATCC, Rockville, Md.) supplemented with 10% fetal calf serum (FCS, Mediatech, Manassas, Va.) Canada), whereas MDA-MB-231 and MCF-7 cells were cultured in EMEM with 10% Fetal Calf Serum and L-glutamine. MG-132 was from Sigma Aldrich (St Louis, Mo.). Colorectal cancer cell lines HCT116 CACO-2, COLO 320, and RKO were cultured in Dulbecco's Modified Eagles Medium (DMEM, Lonza, Basel, Switzerland). K562, and colorectal cancer cell line LS-174T was cultured in Roswell Park Memorial Institutes (RPMI, Lonza, Basel, Switzerland) medium. All cell culture media were supplemented with 100 U/mL penicillin, 100 mg/mL streptomycin (Life technologies, Bleiswijk, NL) and 10% Fecal Calf Serum (FCS, Sigma-Aldrich, St. Louis, USA). Cells were maintained at 37° C. in a 5% CO$_2$ humidified setting.

Detection of phosphatase enzymatic activity. Fluorescent polarization assay (Echelon Biosciences, Salt Lake City, Utah) was used. Recombinant SHIP1 or SHIP2 was mixed with its substrate PtdIns(3,4,5)P$_3$ in the presence of potential chemical inhibitors. The reaction product was mixed with PtdIns(3,4)P$_2$ detector protein and a fluorescent PI(3,4)P$_2$ probe. Newly synthesized PtdIns(3,4)P$_2$ displaces the detector protein, thereby enhancing unbound fluorescent probe in the mixture and decreasing mean polarization units (mPu). Thus identified SHIP inhibitors, 2-phenyl-(-2-piperidinyl-benzol[h]quinoline-4-methanol (1PIE), 1-[(chlorophenyl) methyl]-2-methyl-5-(methylthio)-1H-Indole-3-ethanamine hydrochloride (2PIQ) and 6,8-dichloro-(-2-piperidinyl-2-tricyclo[3.3.1.13,7]dec-1-yl-4-quinolinemethanol hydrochloride (6PTQ) were subsequently tested for inhibition of free phosphate production by recombinant SHIP1 or SHIP2 (Echelon Biosciences) by Malachite Green assay (Echelon Biosciences, Salt Lake City, Utah) by fluorescent polarization assay. To demonstrate selectivity of the compounds for SHIP1 and SHIP2 over other phosphatases, SHIP1 and the inositol 5-phosphatase OCRL were immuno-precipitated from OPM2 cells. For this purpose, OPM2 cells were lysed in IP-lysis buffer (20 mM Tris, 150 mM NaCl, 1 mM EDTA, 1 mM EGTA, 1% Triton X100, 1 mM PMSF, Halt protease inhibitor), and SHIP1 or OCRL were immuno-precipitated using mouse IgG antibodies from Santa Cruz Biotechnology (Santa Cruz, Calif.). Beads were washed four times with IP lysis buffer and once with TBS/MgCl$_2$ (10 mM) and resuspended in TBS/MgCl$_2$. SHIP inhibitors (200 μM) were added to the beads for 5 minutes, after which immunoprecipitated SHIP1 was incubated in the presence of 100 μM PtdIns(3,4,5)P$_3$ (Echelon Biosciences, Salt Lake City, Utah), whereas immunoprecipitated OCRL was incubated in the presence of 100 μM PtdIns(4,5)P$_2$ for 30 minutes. Malachite green solution was added according to manufacturer's instructions, and the plate was read after 20 minutes. Identification of 3α-aminocholestane (3AC) was described previously.

Cell viability assay. Cell viability was assessed using MTT assays. Cells were incubated with different concentrations of SHIP2 inhibitors, and/or chemotherapeutic agent 5-FU. 24 h, 48 h, 72 h, and 96 h after incubation cells were incubated with 5 mM MTT (3-(4,5-Dimethylthiazol-2-yl)-2,5-diphenyltetrazolium bromide) for 3 h and colorimetric changes were measured using a microplate reader (Model 680XR Bio-Rad) at 490 and 595 nm.

Western blotting. HCT116 and CACO-2 cells were serum starved by incubating for 2 h, after which cells were stimulated for 15 minutes with EGF (10 ng/mL), or stimulated for 1 h with LY2940002 (20 μM) or SHIP2 inhibitor K149 (10 μM). Subsequently, cells were washed with PBS and lysed on ice in 300 μL 2× concentrated Laemmli buffer (100 mM Tris-HCl (pH 6.8), 200 mM dithiothreitol, 4% SDS, 0.1% bromophenol blue, 20% glycerol, and 2% DTT) and boiled for 5 minutes at 95° C. Cell extracts were resolved by SDS-PAGE and transferred to polyvinylidene difluoride membranes (Merck chemicals BV, Amsterdam, the Netherlands). Membranes were blocked in 50% odyssey blocking buffer (LI-COR Biosciences, Lincoln, Nebr.) in PBS/0.05% Tween-20 and incubated overnight at 4° C. with primary antibody. After washing in PBS-T, membranes were incubated with IRDye® antibodies (LI-COR Biosciences, Lincoln, Nebr.) for 1 h. Detection was performed using Odyssey reader and analyzed using manufacturers software.

Statistical Analysis. Statistical analysis was performed using either GraphPad Prism 5 or SPSS 17 software. The effect of inhibitors on cell viability was determined by Student T-test for paired samples and comparisons between inhibitors done by independent samples T-test. Increases in Annexin V positive cells upon treatment with inhibitors was calculated by Student T-test for paired samples. Mouse survival curves were compared by Log-rank (Mantel-Cox) Test.

Figure 1B:
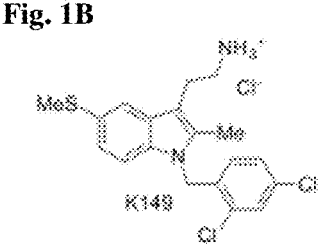
Figure 1C:
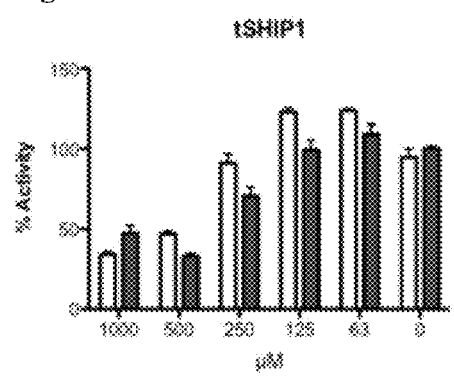
FIG. 1E shows a bar graph of the data from FIG. 1C and FIG. 1D together.
Figure 1D:
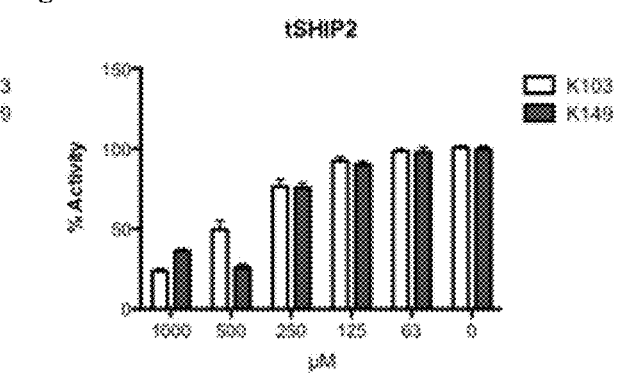
Figure 1E:
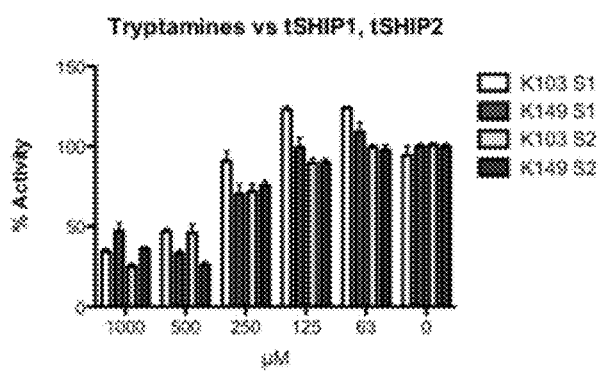
Figure 2A:
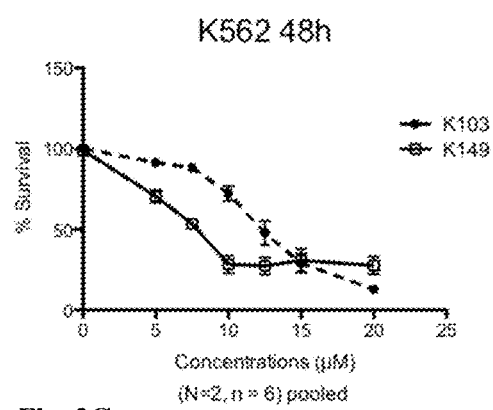
FIGS. 2A-D are line graphs showing the effect of K149 on cell growth in FIG. 2A K562, FIG. 2B OPM2, FIG. 2C MCF-7, FIG. 2D MDA-MB-231 cell lines. Cells were treated in triplicate or more with increasing concentrations of compounds.
Figure 2B:
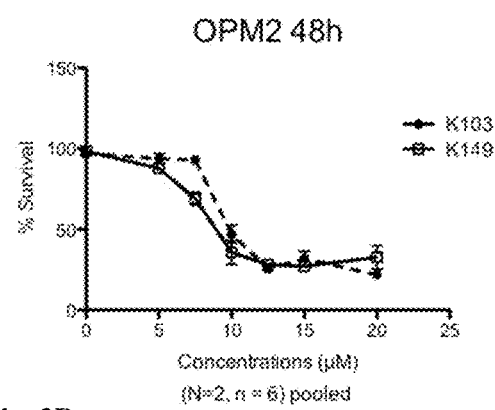
Figure 2C:
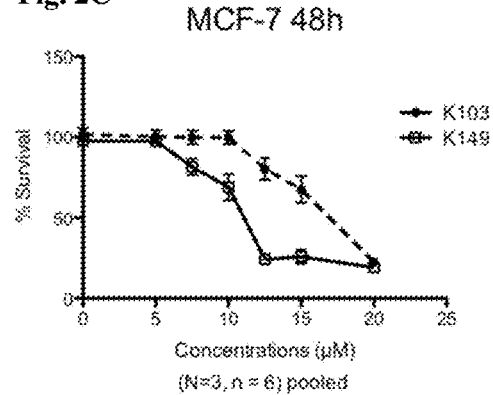
Figure 2D:
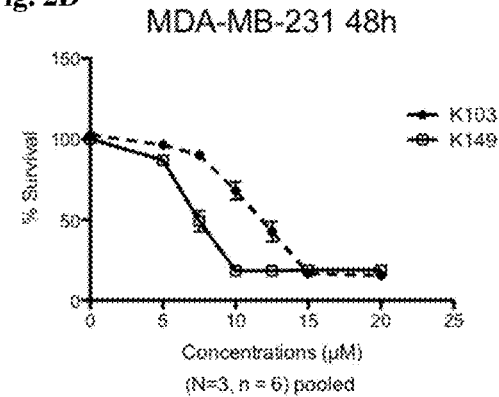

While K103 has been shown to be effective in killing breast cancer cells, it was surprising that compounds of the present disclosure (such as K149) had superior effects compared to K103. (FIG. 1A-C).

After K149 showed activity against SHIP2 (FIG. 1A-C, FIG. 5), it was tested against a number of cancer cell lines, including breast cancer cell lines (MCF-7 and MDA-MB-231 are breast cancer cell lines, K562 is a leukemia cell line and OPM2 is a multiple myeloma cell line). K149 was more effective at controlling cancer cell growth in these cancer cell lines than K103 (FIG. 2A-D).

Figure 3A:
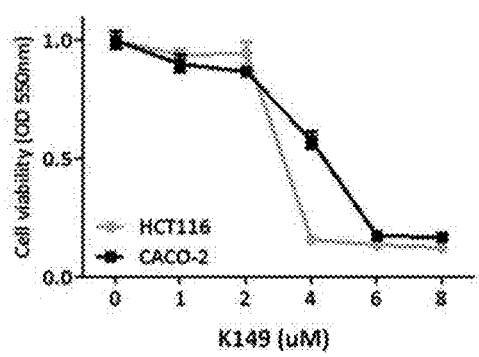
FIGS. 3A-B are line graphs showing the effect of K149 (FIG. 3A) and K103 (FIG. 3B) on cell viability in colorectal cancer cell lines HCT116 and CACO-2.
Figure 3B:
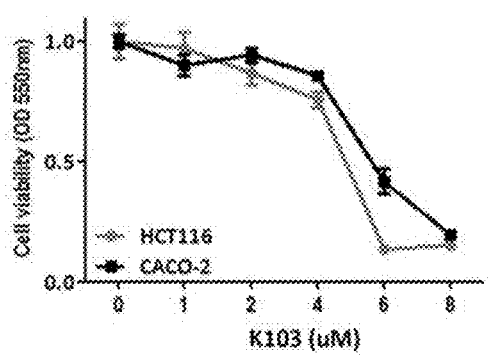
Figure 3C:
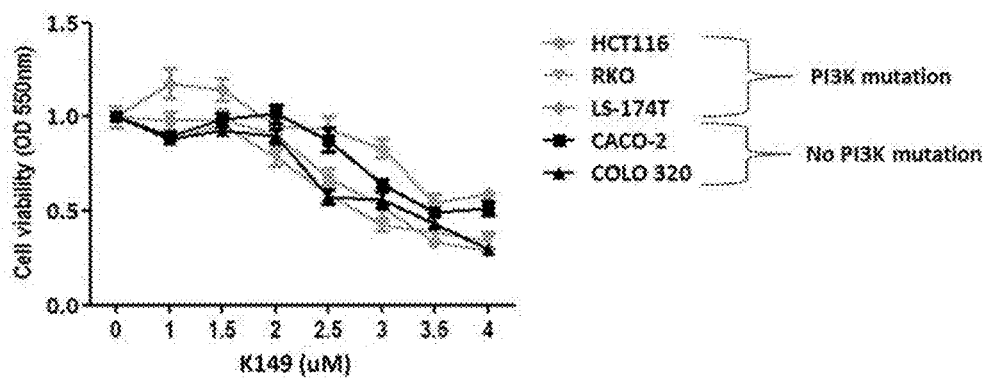
FIG. 3 is a line graph showing the effect of K149 on cell viability in cell lines with PI3K mutations (HCT116, RKO, and LS-174T) and without PI3K mutations (CACO-2 and COLO 320). Treatment of HCT116 and CACO-2 colorectal cancer cell lines with two different SHIP2 activity inhibitors (K149 and K103) results in a dose-dependent cell death. Since CACO-2 cells seem to be more resistant to SHIP2 inhibition, other cell lines with PI3K-mutations were tested. No relationship between SHIP2 inhibition and PI3K mutational status exists.

Recent results now show that K149 is also better at killing colorectal cancer cell lines. MTT assays were performed in 2 different epithelial colorectal cancer cell lines (HCT116 and CACO-2) with two different SHIP2 inhibitors (K103 (formerly 2PIQ)) and K149. While both compounds induced a dose-dependent reduction in cell viability, both cell lines were more sensitive to the K149 inhibitor (FIG. 3A-B). Furthermore, both inhibitors induced cell death at lower concentrations in HCT116 cells than CACO-2 cells. Although both cell lines originate from human colorectal cancers, they have a very different mutational profile, with HCT116 cells harboring a H1047R mutation in PIK3CA gene, whereas CACO-2 cells do not. Since it has been previously shown that mutations in the PIK3CA gene confer differential sensitivity to drugs targeting the PI3K-PKB-pathway, we wondered whether this could also be true for the difference we observed with our SHIP2 inhibitors. However, upon comparison of 5 different cell lines (3 with PIK3CA mutation, 2 without) no difference in sensitivity to SHIP2 inhibition based on PIK3CA mutational status was observed (FIG. 3C). This suggests that SHIP2 inhibitors might be a universal target for treatment of CRC, irrespective of genetic background.

Figure 4A:
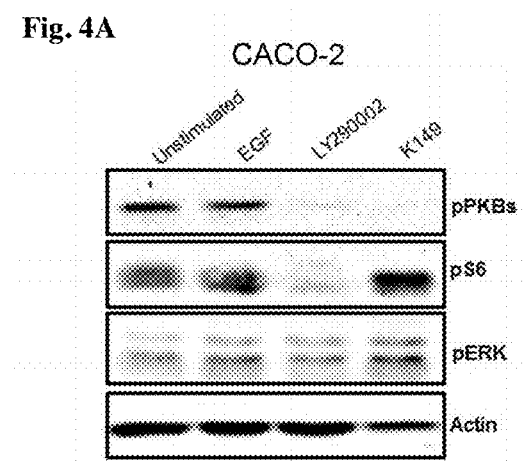
FIGS. 4A-B are immunoblots of CACO-2 (FIG. 4A) and HCT116 (FIG. 4B) cells treated with K149. Phosphorylated PKB, pS6, and ERK were detected. Treatment of CACO-2 and HCT116 cells with K149 results in decreased PKB phosphorylation, and increased pS6 phosphorylation. In contrast, control treatment with the PI3K inhibitor LY2940002 reduces both PKB phosphorylation and its downstream target pS6. ERK phosphorylation is affected by neither inhibitor.
Figure 4B:
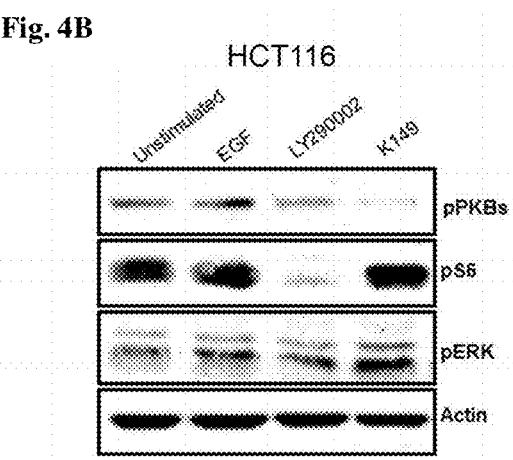
Figure 4C:
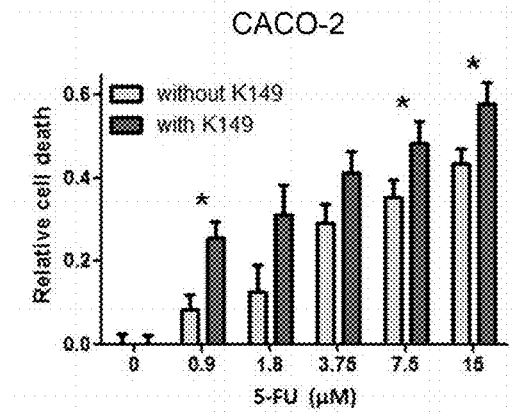
FIG. 4C-D are bar graphs showing the effect of K149 on 5-FU-induced cell death in CACO-2 (FIG. 4C) and HCT116 (FIG. 4D) cell lines. In the presence of low concentrations of SHIP2 inhibitor, 5-FU-induced cell death is enhanced, in particular with low concentrations of 5-FU (*P<0.05).
Figure 4D:
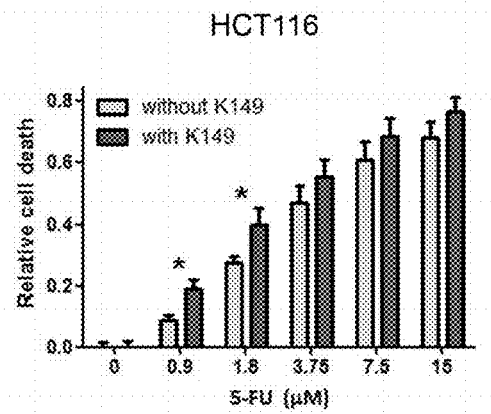
Figure 5:
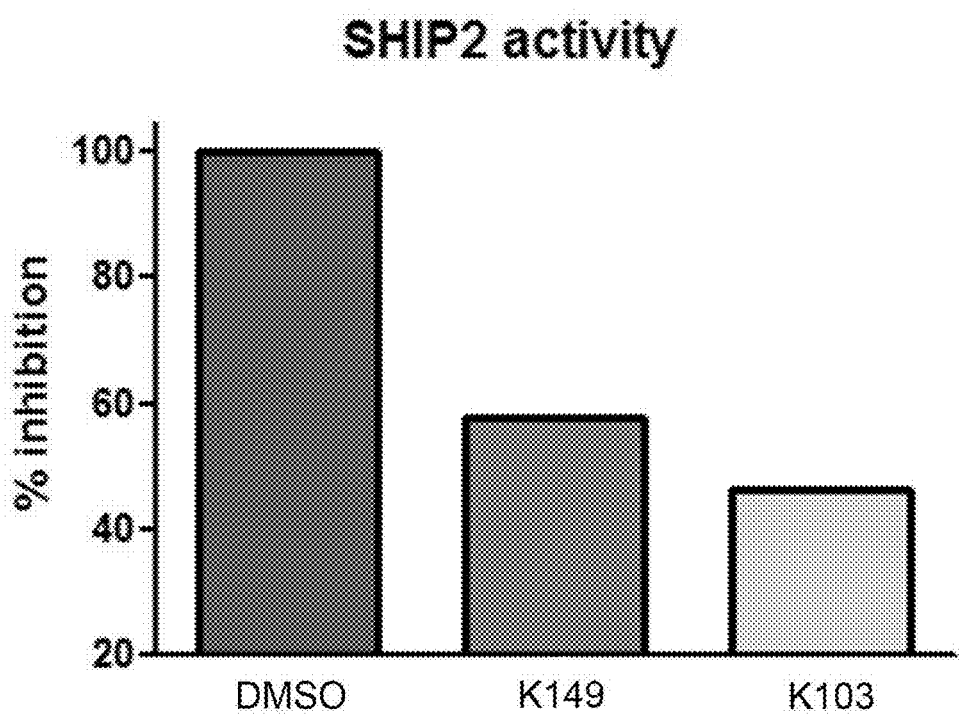
FIG. 5 is a bar graph showing the inhibition of SHIP2 activity by K149 and K103. Recombinant SHIP2 was incubated with vehicle control (DMSO) or 500 uM of the SHIP2 inhibitors K149 and K103, showing inhibition of the SHIP2 activity.

Since we observed a steep decrease in cell viability upon SHIP2 inhibition, we examined the effect of SHIP2 inhibition on the downstream signaling involved in processes like proliferation and cell survival (FIG. 4A-B). Epidermal Growth Factor (EGF) activates cellular signaling as shown by increased protein phosphorylation of PKB, ribosomal protein S6 and ERK. The PI3K inhibitor LY294002 inhibits activity of PKB and its downstream target ribosomal S6 protein. SHIP2 inhibition however, results in diminished phosphorylation of PKB, while phospho-S6 levels are drastically increased. ERK phosphorylation levels were not affected by either inhibitor, demonstrating their specificity. Together these data suggest that SHIP2 can affect mTOR signaling, independent of PKB. Since SHIP2 inhibition reduces PKB phosphorylation, we speculated that this reduced survival signal would sensitize cells to chemotherapeutic agents. When we treated intestinal epithelial cells with a low dose of the SHIP2 inhibitor K149 (2 uM), together with increasing concentrations of 5-FU, it was apparent that co-treatment with the SHIP2 inhibitor sensitizes CRC cells to the 5-FU treatment (FIG. 4C-D). This suggests that chemical SHIP2 inhibition would be a worthwhile addition to the standard chemotherapy regimen, requiring lower concentrations of chemotherapeutics to achieve the same amount of tumor cell killing.

Example 3

This example provides comparative data for some compounds described herein with respect to inhibition of SHIP1 and SHIP2. Effect on SHIP1 and SHIP2 inhibition was determined as described in Example 2.

TABLE 1

In vitro SHIP Inhibition of Selected Compounds

| Compound | SHIP1 Inhibition[a] | SHIP2 Inhibition[a] |
| --- | --- | --- |
| K123 | 15% | nd[b] |
| K124 | 62% | 70% |
| K125 | 64% | 80% |
| K148 | 77% | 70% |
| K149 | 81% | 57% |
| K160 | 78% | 61% |

[a]Tested against the phosphatase in the Malachite green assay at 1mM
[b]nd = not determined Example 4

This example describes the effect of K149 on host and donor T cell function.

Mice were dosed for 6 days with K149 (10 mg/kg in 5% DMSO) and the indicated cell numbers and frequencies were determined by flow cytometry in FIG. 7A-D. Results show that K149 administration leads to significant increases in MDSC, iTreg cells, nTreg cells, and neutrophil counts.

Example 5

This example describes the effect of the compositions of the present disclosure on obesity and related parameters.

Mice were maintained on a high fat diet (HFD, containing 45% kcal % fat; Research Diets, Inc., NJ, Product Data D12451), prior to treatment with K149 and then treated with K149 (2× week, i.p., 10 mg/kg) for two weeks while continuing to consume a HFD. Their weight was measured at the end of the two week treatment period.

Both total weight and % body weight of the K149 mice showed significant reductions despite continued consumption of a HFD. (*p<0.05, ***p<0.001) The K149 mice showed reduced body weight vs. vehicle mice weighed after the 2 week treatment and vs. their own weight as measured prior to K149 treatment.

To determine the effect of the present compositions on bone health, mice were maintained on a high fat diet (HFD) prior to treatment with K149 and then treated with K149 (2× week, i.p., 10 mg/kg) for two weeks while continuing to consume a HFD. Their bone mineral density (BMD) and bone mineral content (BMC) was then was measured at the end of the two week treatment period by dual-energy x-ray absorptiometry (DEXA) The K149 mice showed no significant reduction or increase in either measure of bone health.

The results indicate that K149 promotes weight loss in diet-induced obese (DIO) mice as well as reverses obesity, despite continued consumption of a high fat diet (FIG. 8A-B and FIG. 9A-B). No toxicity was observed with this K149 treatment.

While the disclosure has been particularly shown and described with reference to specific embodiments, it should be understood by those having skill in the art that various changes in form and detail may be made therein without departing from the spirit and scope of the disclosure.

REFERENCES

1. Siegel R, Desantis C, Jemal A. Colorectal cancer statistics, 2014. CA Cancer J Clin [Internet]. 2014; 64:104-17.
2. Van Cutsem E, Köhne C-H, Hitre E, Zaluski J, Chang Chien C-R, Makhson A, et al. Cetuximab and chemotherapy as initial treatment for metastatic colorectal cancer. N Engl J Med. 2009; 360(14):1408-17.
3. Folprecht G, Gruenberger T, Bechstein W O, Raab H R, Lordick F, Hartmann J T, et al. Tumour response and secondary resectability of colorectal liver metastases following neoadjuvant chemotherapy with cetuximab: the CELIM randomised phase 2 trial. Lancet Oncol. 2010; 11(1):38-47.
4. Douillard J Y, Siena S, Cassidy J, Tabernero J, Burkes R, Barugel M, et al. Final results from PRIME: randomized phase III study of panitumumab with FOLFOX4 for first-line treatment of metastatic colorectal cancer. Ann Oncol [Internet]. 2014; 25(7):1346-55.
5. Seshacharyulu P, Ponnusamy M P, Haridas D, Jain M, Ganti A K, Batra S K. Targeting the EGFR signaling pathway in cancer therapy. Expert Opinion on Therapeutic Targets. 2012. p. 15-31.
6. Han C-B, Li F, Ma J-T, Zou H-W. Concordant KRAS Mutations in Primary and Metastatic Colorectal Cancer Tissue Specimens: A Meta-Analysis and Systematic Review. Cancer Investigation. 2012. p. 121017084328003.
7. Liévre A, Bachet J B, Le Corre D, Boige V, Landi B, Emile J F, et al. KRAS mutation status is predictive of response to cetuximab therapy in colorectal cancer. Cancer Res. 2006; 66(8):3992-5.
8. Grothey A, Van Cutsem E, Sobrero A, Siena S, Falcone A, Ychou M, et al. Regorafenib monotherapy for previously treated metastatic colorectal cancer (CORRECT): an international, multicentre, randomised, placebo-controlled, phase 3 trial. Lancet [Internet]. 2013; 381(9863): 303-12.
9. Wong K K, Engelman J A, Cantley L C. Targeting the PI3K signaling pathway in cancer. Current Opinion in Genetics and Development. 2010. p. 87-90.
10. Fuhler, G. M.; Brooks, R.; Toms, B.; Iyer, S.; Gengo, E. A.; Park, M. Y.; Gumbleton, M.; Viernes, D. R.; Chisholm, J. D.; Kerr, W. G. Therapeutic potential of SH2 domain-containing inositol-5'-phosphatase 1 (SHIP1) and SHIP2 inhibition in cancer. Mol. Med. 2012, 18, 65-75. doi:10.2119/molmed.2011.00178

What is claimed is:

1. A method for treating a condition selected from the group consisting of cancer, obesity, diabetes and metabolic syndrome in a subject in need thereof, the method comprising administering to the subject a composition comprising an effective amount of a compound having a formula selected from the group consisting of:

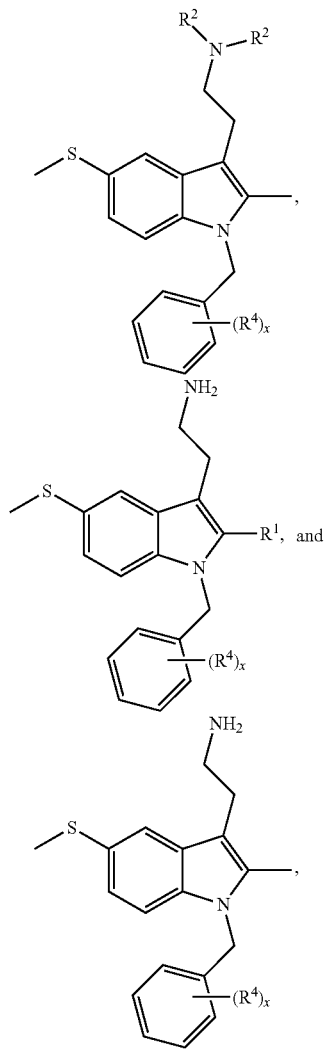

wherein,
$R^1$ is selected from the group consisting of H, $C_{1-4}$ alkyl, and $C_{5-6}$ aryl;
each $R^2$ is independently selected from the group consisting of H, $C_{3-4}$ alkyl, and $C_{5-6}$ aryl;

R⁴ is halo, and x is 0 or 2-5, and pharmaceutically acceptable esters, salts, and prodrugs thereof.

2. The method of claim 1, wherein the compound is selected from the group consisting of:

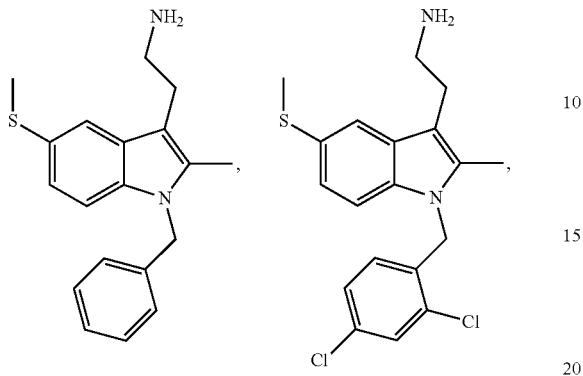

and pharmaceutically acceptable esters, salts, and prodrugs thereof.

3. The method of claim 1, wherein the cancer is breast cancer, colorectal cancer, glioblastoma, osteosarcoma, neuroblastoma, lymphoma, multiple myeloma, leukemia, or cancers of epithelial tissue origin.

4. The method of claim 1, wherein the subject is obese, has diabetes or has metabolic syndrome.

5. The method of claim 1, wherein $R^1$ is one of $C_{1-4}$ alkyl and $C_{5-6}$ aryl.

* * * * *